United States Patent
Lee

(10) Patent No.: US 11,427,839 B2
(45) Date of Patent: Aug. 30, 2022

(54) YEAST STAGE TANK INCORPORATED FERMENTATION SYSTEM AND METHOD

(71) Applicant: Lee Tech LLC., San Jose, CA (US)

(72) Inventor: Chie Ying Lee, San Jose, CA (US)

(73) Assignee: Lee Tech LLC, Los Gatos, CA (US)

( * ) Notice: Subject to any disclaimer, the term of this patent is extended or adjusted under 35 U.S.C. 154(b) by 0 days.

(21) Appl. No.: 17/067,701

(22) Filed: Oct. 11, 2020

(65) Prior Publication Data

US 2021/0024964 A1 Jan. 28, 2021

Related U.S. Application Data

(63) Continuation-in-part of application No. 14/839,763, filed on Aug. 28, 2015.

(60) Provisional application No. 62/044,092, filed on Aug. 29, 2014, provisional application No. 62/914,276, filed on Oct. 11, 2019.

(51) Int. Cl.
| | |
|---|---|
| *C12P 7/14* | (2006.01) |
| *C12M 1/00* | (2006.01) |
| *C12P 1/06* | (2006.01) |
| *C12P 7/00* | (2006.01) |
| *C12P 5/00* | (2006.01) |
| *C12N 1/18* | (2006.01) |
| *C12R 1/85* | (2006.01) |

(52) U.S. Cl.
CPC .............. *C12P 7/14* (2013.01); *C12M 23/58* (2013.01); *C12N 1/185* (2021.05); *C12P 1/06* (2013.01); *C12P 5/00* (2013.01); *C12P 7/00* (2013.01); *C12N 2511/00* (2013.01); *C12R 2001/85* (2021.05)

(58) Field of Classification Search
CPC ...... C12P 7/14; C12P 1/06; C12P 5/00; C12P 7/00; C12M 23/58; C12R 1/85; C12R 2001/85; C12N 2511/00; C12N 1/185; C12N 2501/00
USPC ......................................................... 435/243
See application file for complete search history.

(56) References Cited

U.S. PATENT DOCUMENTS

| | | |
|---|---|---|
| 1,942,943 A | 1/1934 | Schnabel |
| 2,190,176 A | 2/1940 | Smith |
| 2,313,275 A | 3/1943 | Schopmeyer |
| 2,600,903 A | 6/1952 | Miller |
| 2,967,107 A | 1/1961 | Geiger et al. |
| 3,054,676 A | 9/1962 | Lauhoff et al. |
| 3,058,887 A | 10/1962 | Platt et al. |
| 3,753,723 A | 8/1973 | Henderson |
| 3,786,078 A | 1/1974 | Smith et al. |
| 3,827,423 A | 8/1974 | Bolitho |
| 3,973,043 A | 8/1976 | Lynn |
| 3,975,546 A | 8/1976 | Stahmann |
| 4,042,172 A | 8/1977 | Norzdrovsky |
| 4,130,553 A | 12/1978 | Batley, Jr. |
| 4,171,383 A | 10/1979 | Chwalek et al. |
| 4,255,518 A | 3/1981 | Muller et al. |
| 4,313,061 A | 1/1982 | Thomas |
| 4,333,871 A | 6/1982 | De Jong |
| 4,341,713 A | 7/1982 | Stolp et al. |
| 4,361,651 A | 11/1982 | Keim |
| 4,396,161 A | 8/1983 | Roukolainen et al. |
| 4,517,022 A | 5/1985 | Harvey |
| 4,635,864 A | 1/1987 | Peterson et al. |
| 4,772,481 A | 9/1988 | Rohwer |
| 4,835,100 A | 5/1989 | Dixon |
| 4,857,325 A | 8/1989 | Albeck |
| 4,978,618 A * | 12/1990 | Kalina .................... C12P 7/14 435/162 |
| 5,177,008 A | 1/1993 | Kampen |
| 5,244,159 A | 9/1993 | Newman |
| 5,248,099 A | 9/1993 | Lahner et al. |
| 5,294,434 A | 3/1994 | King |
| 5,364,335 A | 9/1994 | Franzen et al. |
| 5,475,099 A | 12/1995 | Knauf |
| 5,516,974 A | 5/1996 | Sasae |
| 5,994,113 A | 11/1999 | Kauppinen et al. |
| 6,080,401 A | 6/2000 | Reddy |

(Continued)

FOREIGN PATENT DOCUMENTS

| | | |
|---|---|---|
| AU | 2013200519 B2 | 2/2013 |
| CN | 1883299 A | 12/2006 |

(Continued)

OTHER PUBLICATIONS

Labedz et al., Precise mass determination of single cell with cantilever-based microbiosensor system, PLOS One, 12(11), (2017), pp. 1-14.*

(Continued)

*Primary Examiner* — Jennifer M. H. Tichy

(74) *Attorney, Agent, or Firm* — Haverstock & Owens, A Law Corporation

(57) ABSTRACT

Methods of and system for growing and maintaining an optimized/ideal active yeast solution in the yeast tank and fermenter tank during the fermentation filling cycle are provided. A new yeast stage tank is used between the yeast tank and the fermenter tank allowing yeast to rapidly produce a huge amount of active young yeast cells for a fermenter during the filling period. A measurable and useful controlling factor, % DT/% Yeast by weight ratio (or "food" to yeast ratio), is used (e.g., % DT=glucose), which offers information on the health status of the yeast. The controlling factor is used to control the status of the yeast throughout the entire process.

12 Claims, 7 Drawing Sheets

(56) References Cited

U.S. PATENT DOCUMENTS

| | | | |
|---|---|---|---|
| 6,190,462 B1 | 2/2001 | Markland et al. | |
| 6,254,914 B1 | 7/2001 | Singh et al. | |
| 6,274,358 B1 | 8/2001 | Holtz et al. | |
| 6,899,910 B2 | 5/2005 | Johnston et al. | |
| 7,297,236 B1 | 11/2007 | Vander Griend | |
| 7,563,469 B1 | 7/2009 | Navarro et al. | |
| 7,700,094 B1 | 4/2010 | Nsereko | |
| 7,858,140 B2 | 12/2010 | Paustian et al. | |
| 9,012,191 B2 | 4/2015 | Lee | |
| 9,388,475 B2 | 7/2016 | Lee | |
| 9,777,303 B2 | 10/2017 | Jakel et al. | |
| 10,190,086 B2 * | 1/2019 | Narendranath | C12N 1/16 |
| 2001/0014360 A1 | 8/2001 | Paluch | |
| 2002/0122944 A1 | 9/2002 | Ogle et al. | |
| 2004/0009160 A1 | 1/2004 | Villamar | |
| 2004/0071757 A1 | 4/2004 | Rolf | |
| 2004/0087808 A1 | 5/2004 | Prevost et al. | |
| 2004/0187863 A1 | 9/2004 | Langhauser | |
| 2004/0258782 A1 | 12/2004 | Hoffman et al. | |
| 2005/0009133 A1 | 1/2005 | Johnston et al. | |
| 2005/0028810 A1 | 2/2005 | Lee | |
| 2005/0100996 A1 | 5/2005 | Lantero, Jr. et al. | |
| 2005/0170067 A1 | 8/2005 | Shao et al. | |
| 2005/0249837 A1 | 11/2005 | Massimio et al. | |
| 2005/0281792 A1 | 12/2005 | Short | |
| 2006/0127453 A1 | 6/2006 | Harel | |
| 2006/0154353 A1 | 7/2006 | Duan | |
| 2006/0292677 A1 | 12/2006 | Ostrander | |
| 2007/0066476 A1 | 3/2007 | Ullmann | |
| 2007/0184159 A1 | 8/2007 | Shima et al. | |
| 2007/0184541 A1 | 8/2007 | Karl et al. | |
| 2007/0210007 A1 | 9/2007 | Scheimann et al. | |
| 2007/0231311 A1 | 10/2007 | Kroening et al. | |
| 2008/0095881 A1 | 4/2008 | Ber | |
| 2008/0210541 A1 | 9/2008 | Wenger et al. | |
| 2009/0029432 A1 | 1/2009 | Abbas et al. | |
| 2009/0093027 A1 | 4/2009 | Balan et al. | |
| 2009/0061490 A1 | 5/2009 | Edwards et al. | |
| 2009/0181153 A1 | 7/2009 | Bendorf et al. | |
| 2009/0227004 A1 | 9/2009 | Dale | |
| 2010/0028484 A1 | 2/2010 | Kriesler et al. | |
| 2010/0082312 A1 | 4/2010 | Macharia | |
| 2010/0093860 A1 | 4/2010 | Boon et al. | |
| 2010/0120128 A1 | 5/2010 | Liang | |
| 2010/0159547 A1 | 6/2010 | Falcounbridge | |
| 2010/0159552 A1 | 6/2010 | Benson et al. | |
| 2010/0196994 A1 | 8/2010 | Van Leeuwen et al. | |
| 2010/0260918 A1 | 10/2010 | Wang | |
| 2010/0324274 A1 | 12/2010 | DeFrees | |
| 2011/0086149 A1 | 4/2011 | Bootsma | |
| 2011/0100359 A1 | 5/2011 | North | |
| 2011/0106277 A1 | 5/2011 | Sayyar-Rodsari | |
| 2011/0123657 A1 | 5/2011 | Vandenbroucke et al. | |
| 2011/0150853 A1 | 6/2011 | Mann et al. | |
| 2011/0177560 A1 | 7/2011 | Galvez, III et al. | |
| 2011/0223307 A1 | 9/2011 | Bertoldo de Barros et al. | |
| 2011/0250310 A1 | 10/2011 | Mateus | |
| 2011/0250312 A1 | 10/2011 | Lewis | |
| 2011/0269185 A1 | 11/2011 | David | |
| 2011/0283602 A1 | 11/2011 | Gallop et al. | |
| 2011/0315541 A1 | 12/2011 | Xu | |
| 2012/0048716 A1 | 3/2012 | Sonnek | |
| 2012/0077232 A1 | 3/2012 | Budaraju et al. | |
| 2012/0077244 A1 | 3/2012 | Budaraju et al. | |
| 2012/0107454 A1 | 5/2012 | Hoffman et al. | |
| 2012/0125859 A1 | 5/2012 | Collins | |
| 2012/0168387 A1 | 7/2012 | Tran et al. | |
| 2012/0183643 A1 | 7/2012 | Dale | |
| 2012/0199531 A1 | 8/2012 | Winsness | |
| 2012/0244590 A1 | 9/2012 | Lee | |
| 2012/0245123 A1 | 9/2012 | Lopez Pedrosa et al. | |
| 2012/0252065 A1 | 10/2012 | Rozenszain et al. | |
| 2012/0270275 A1 | 10/2012 | Fenton et al. | |
| 2013/0121891 A1 | 5/2013 | Dieker | |
| 2013/0130343 A1 | 5/2013 | Purtle et al. | |
| 2013/0224333 A1 | 8/2013 | Nanjundaswamy et al. | |
| 2013/0236936 A1 | 9/2013 | Lee | |
| 2013/0288376 A1 | 10/2013 | Lee | |
| 2013/0206342 A1 | 11/2013 | Dahmes | |
| 2013/0316041 A1 | 11/2013 | Maranz | |
| 2013/0337517 A1 | 12/2013 | Razavi-Shirazi et al. | |
| 2013/0344045 A1 | 12/2013 | Faure | |
| 2014/0004571 A1 | 1/2014 | Garrett | |
| 2014/0053829 A1 | 2/2014 | Lee | |
| 2014/0102950 A1 | 4/2014 | Bethke | |
| 2014/0186868 A1 | 7/2014 | Siegert | |
| 2014/0206055 A1 | 7/2014 | Ramos | |
| 2014/0242251 A1 | 8/2014 | Bootsma | |
| 2014/0273140 A1 | 9/2014 | Langhouser | |
| 2014/0319066 A1 | 10/2014 | LoCascio | |
| 2014/0343254 A1 | 11/2014 | Gerardi | |
| 2015/0152372 A1 | 6/2015 | Kohl | |
| 2015/0176034 A1 | 6/2015 | Ramos | |
| 2015/0223493 A1 | 8/2015 | Lee | |
| 2015/0231535 A1 | 8/2015 | Lee | |
| 2015/0240266 A1 | 8/2015 | Lee | |
| 2015/0307822 A1 | 10/2015 | Rossell et al. | |
| 2016/0060658 A1 | 3/2016 | Lee | |
| 2016/0374364 A1 | 12/2016 | Lee | |
| 2017/0058300 A1 | 3/2017 | Aurandt | |
| 2018/0225669 A1 | 8/2018 | Brotherson | |
| 2019/0017080 A1 | 1/2019 | Bootsma | |
| 2019/0241834 A1 | 8/2019 | Lee | |

FOREIGN PATENT DOCUMENTS

| | | |
|---|---|---|
| CN | 1966706 A | 5/2007 |
| CN | 101080483 A | 11/2007 |
| CN | 101453884 A | 8/2009 |
| CN | 101621935 A | 1/2010 |
| CN | 101795578 A | 8/2010 |
| CN | 104703957 A | 6/2015 |
| DE | 4239342 A1 | 5/1994 |
| EP | 0772978 B1 | 11/1991 |
| GB | 511525 A | 8/1939 |
| GB | 852995 A | 11/1960 |
| WO | 01/14595 A2 | 3/2001 |
| WO | 2012075481 A1 | 6/2012 |
| WO | 2012145230 A1 | 10/2012 |
| WO | 2012160191 A2 | 11/2012 |
| WO | 2012166290 A1 | 12/2012 |
| WO | 2013034747 A1 | 3/2013 |
| WO | 2014031700 A2 | 2/2014 |
| WO | 20140127852 A2 | 8/2014 |
| WO | 2016033548 A1 | 3/2016 |

OTHER PUBLICATIONS

The Office Action from the Canadian Patent Application No. 2,951,715 dated Aug. 28, 2020.

International Search Report and Written Opinion from PCT Application No. PCT/US15/47577.

"Organic" organic.org; published Dec. 25, 2012, accessed on Mar. 3, 2017, available at htt://web.archive.org/web/20121225201858/http://www.organic.org/home /faq.

Alfagreen supreme: available at:https://web.archive.org/web/20121207054090 2/thttp://www.alfagreensupreme.com. ourproducts:html:published Jul. 12, 2012, accessed on Mar. 6, 2017.

Egg, whole,raw, fresh form composition of Foods Raw, Processed, Prepared , USDA National Nutrient Database for Standard Reference, Release 22, Sep. 2009,; available at :http:// www.ars.usda.gov/northweast-area/beltsville-human-nutrition-research-center/nutrient-data-laboratory/docs/sr22-download-files/: access on Oct. 17, 2017.

Swiss chard, What's New and Beneficial About Swiss Chard: The World's Healthiest Foods; available at: http://web.archive.org/web/20130117060212/http://www.whfoods.com/genpage.php?tname=foodspice&dbid=16;published on Jan. 17, 2013: accessed on Oct. 19, 20174.

Singh et al., Effect of Corn Oil on Thin Stillage Evaporators,Cereal Chemistry, pp. 846-849, 1999.

(56) References Cited

OTHER PUBLICATIONS

Blog, Birdworms & Buttermilk, Extracting Chlorophyll from Leafy Greens; available at: http://birdworms.com/2010/06/26/extractingchlorophyllfromleafygreens/; accessed on Oct. 6, 2016; published on Jun. 2010.

Timbekova et al.., Chemistry and Biological Activity of Triterpenoid glycosides from Medicago.

Gonzalez-Martin, Use of NIRS technology with a remote reflectance fibre-optic probe for predicting mineral composition(Ca, K, P, Fe, Mn, Na, Zn), protein and moisture in alfalfa; Anal Bioanal Chem (2007) 387:2199-2205.

What Are Enzymes?: published Mar. 7, 2013; available at: https://web.archive.org./webs/20130307025120/hrrp://www.enzyme-facts.com/enzymes.html; accessed on Aug. 11, 2017.

"Hydrocarbon." In The Columbia Encyclopedia, by Paul Lagasse, and Columbia University. 7th ed. Columbia University Press, 2017. http://search.credoreference.com/content/entry/columency/hydrocarbon/0?institutionId=743.

"Starch." In The American Heritage (R) Dictionary of the English Language, edited by The Editors of the American Heritage Dictionaries. 5th ed. Houghton Mifflin, 2011. http://search.credoreference.com/content/entry/hmdictenglang/starch/0?institutionId=743.

Kung, A review on silage additives and enzymes, Proceeding of the 59th Minneapolis Nutrition Conference, Sep. 1998; p. 121-135.

Heist, A Guide to Successful Yeast Propagatiion, Ethanol Producer Magazine, 2008.

Dotty 1, New natural medical antibiotic; Chlorophyll & Spinach, available at http://www.acne.org/messageboard/topic/254668-new-natural-medical-antibiotic-chlorophyllspinach/; published Nov. 30, 2009; accessed on Jul. 3, 2017.

Spinach, vol. 1, No. 14, University of the District of Columbia, Center for Nutrition, Diet and Health, published Jan. 23, 2014, accessed on Jul. 30, 2017, available at : https://web.archive.org/web/20140123214335/https://www.udc.edu/docs/causes/online/Spinach%2014.pdf.

Shahina Z. et al., "Variation of Protease Production by the Bacteria (*Bacillus fastidiosus*) and the Fungus (*Aspergillus funiculosus*)", Journal of Microbiology Research [online], 2013 [retrieved on Oct. 17, 2016], vol. 3, issue 4, retrieved from the Internet: <DIO: 10.5923//j.microbiology.2013030402>, pp. 135-142, see entire documents, especially p. 135.

International Search Report from PCT/US16/38436 dated Oct. 31, 2016.

The International Search Report dated Dec. 18, 2018, for International Application No. PCT/US18/56340.

The Office Action for Canadian Patent Application No. 2,951,715 dated Jul. 9, 2019.

The Office Action for Brazilian Patent Application No. BR112015003793-3 dated Jul. 23, 2019.

The Office Action dated May 9, 2019 for Canadian Patent Application No. 2,882,173.

The Brazilian Office Action for Patent Application No. BR112017016172-9 Dated: 26, 2019.

The Brazilian Office Action for Patent Application No. BR112017027884-7 dated Jan. 2, 2020.

The International Preliminary Report form PCT Application No. PCT/US2018/056340, dated Apr. 30, 2020.

The Chinese Office Action dated Jun. 3, 2020 for Chinese Patent Application No. 201680007372.4.

GESE Success, Letters Educational, UK, 2006, p. 19 ( Year: 2006).

The Office Action for the Argentina Patent Application No. 20160101901 dated Aug. 19, 2020.

The Brazilian Office Action dated Aug. 8, 2020 for Brazilian Patent Application No. BR112017004017-4.

The Office Action from the Argentinian Patent Application No. 20160101901 dated Aug. 19, 2020.

The International Search Report and Written Opinion for the Application No. PCT/US20/55174 dated Mar. 18, 2021.

Xu et al., Continuous ethanol production using self-flocculating yeast in a cascade of fermentors Enzyme and Microbial Technology 37 (2005) 634-640, entire document esp p. 635-636.

https://en.wikipedia.org/windex.php?title=Clean-in-place&oldid=889731953'Clean-inplace'Mar. 27, 2019, entire document esp p. 2.

The Office Action dated Dec. 4, 2020, for Chinese Patent Application No. 201680003607.2.

The International Search Report and Written Opinion for the International Application No. PCT/US2020/057558 dated Jan. 27, 2021.

The Office Action for the Chinese Application No. 201680007372.4 dated Feb. 22, 2021.

The Office Action for the Brazilian Patent Application No. BR 11 2015 003793-3 dated Feb. 2, 2021.

Best way to keep dog food and treats fresh—Vacuum seal!,vacmasterfresh.com, Aug. 26, 2015 [online], [retrieved Feb. 11, 2021]. Retrieved from the Internet<https://www.vacmasterfresh.com/fresh-bites-blog/ best-way-to-keep-dog-food-and-treats-fresh-vacuum-seal/>(Year:2015).

The Pelleting Process, California Pellet Mill Co., May 17, 2017[online], [retrieved Feb. 11, 2021]. Retrieved from the Internet<https://www.cpm.net/downloads/ Animal%20Feed%20Pelleting.pdf>(Year:2017).

Vibrating Fluid Bed Dryers, Carrier Vibrating, May 12, 2017[online], [retrieved Feb. 17, 2021].Retrieved from the Internet<https://www.carriervibrating.com/equipment/dryers/vibrating/>(2017).

Imran M. et al., Role of Enzymes in Animal Nutrition: A Review, PSM Vet. Res., 01(2)(2016): 38-45. (Year: 2016).

How many different chemical reactions ca a single enzyme catalyze? ,Truong-Son N, Jan. 3, 2016 [online], [retrieved Mar. 4, 2021]. Retrieved from the Internet<https://socratic.org/questions/jo-many-different-chemical-reactions-can-a single-enzyme-catalyze>(Year:2016).

\* cited by examiner

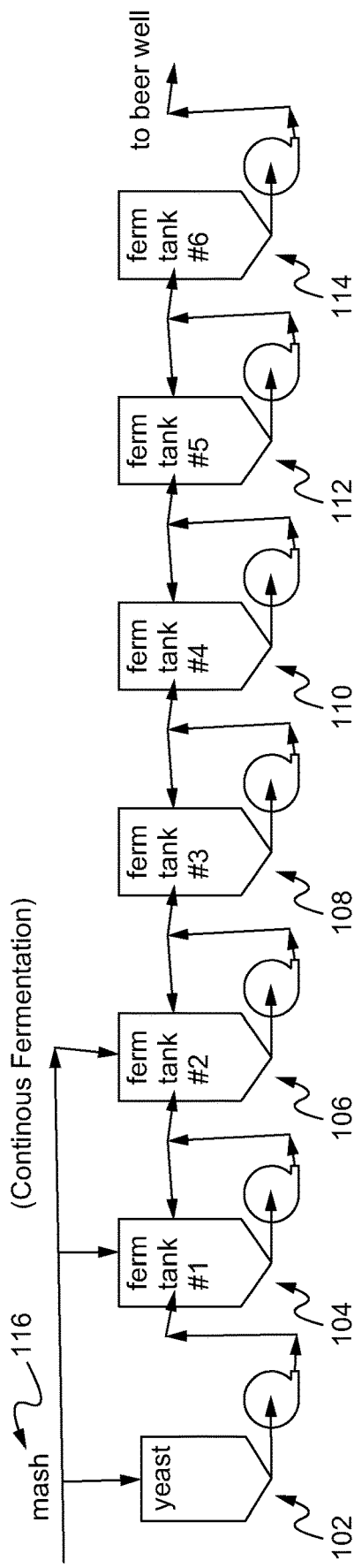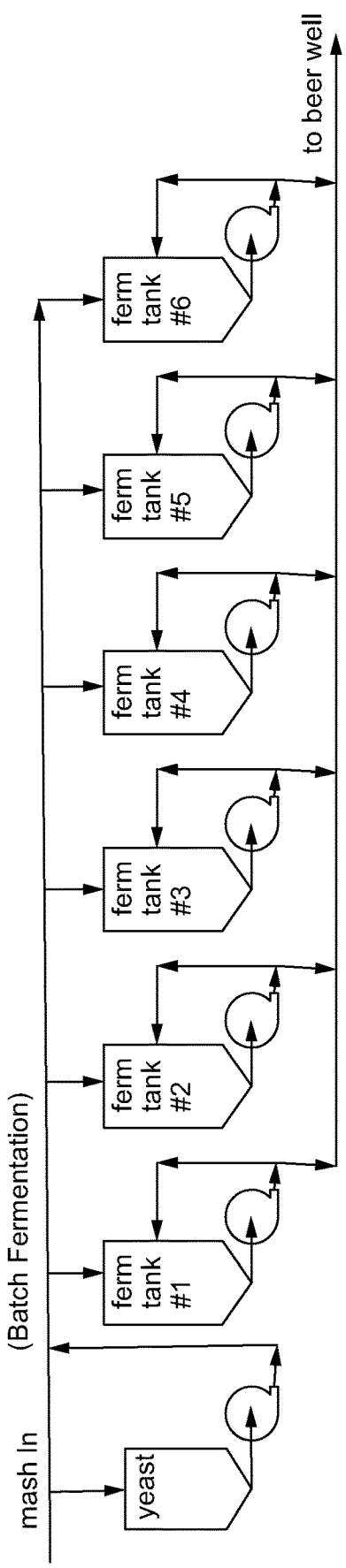

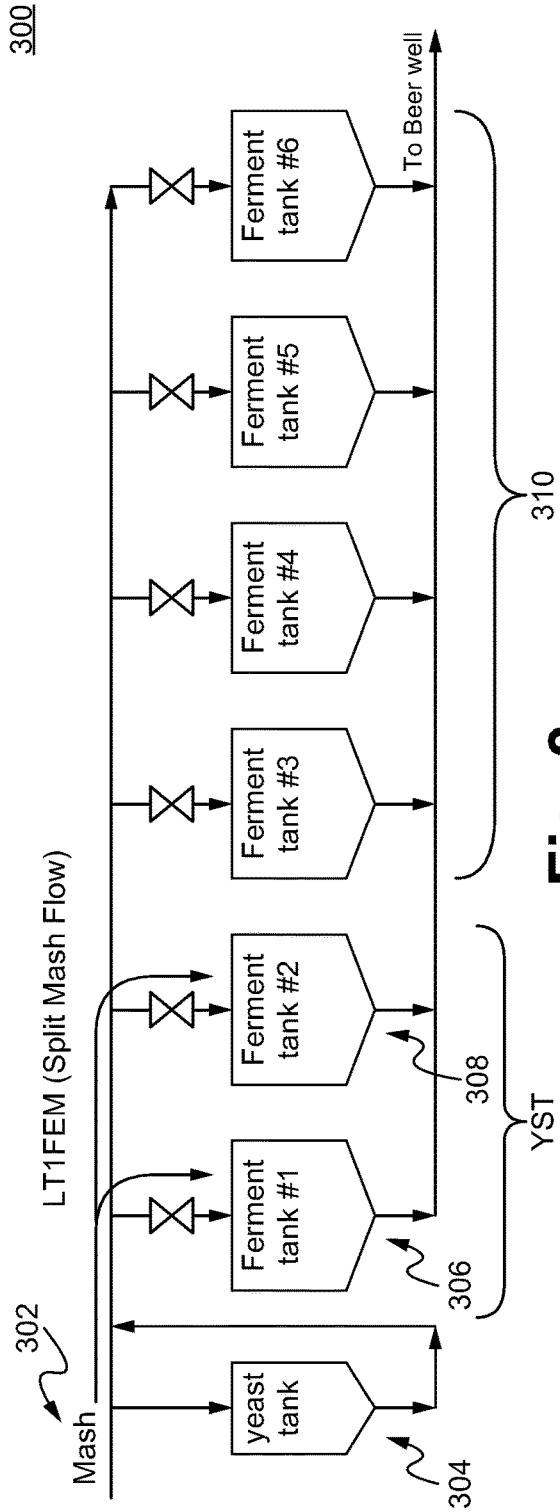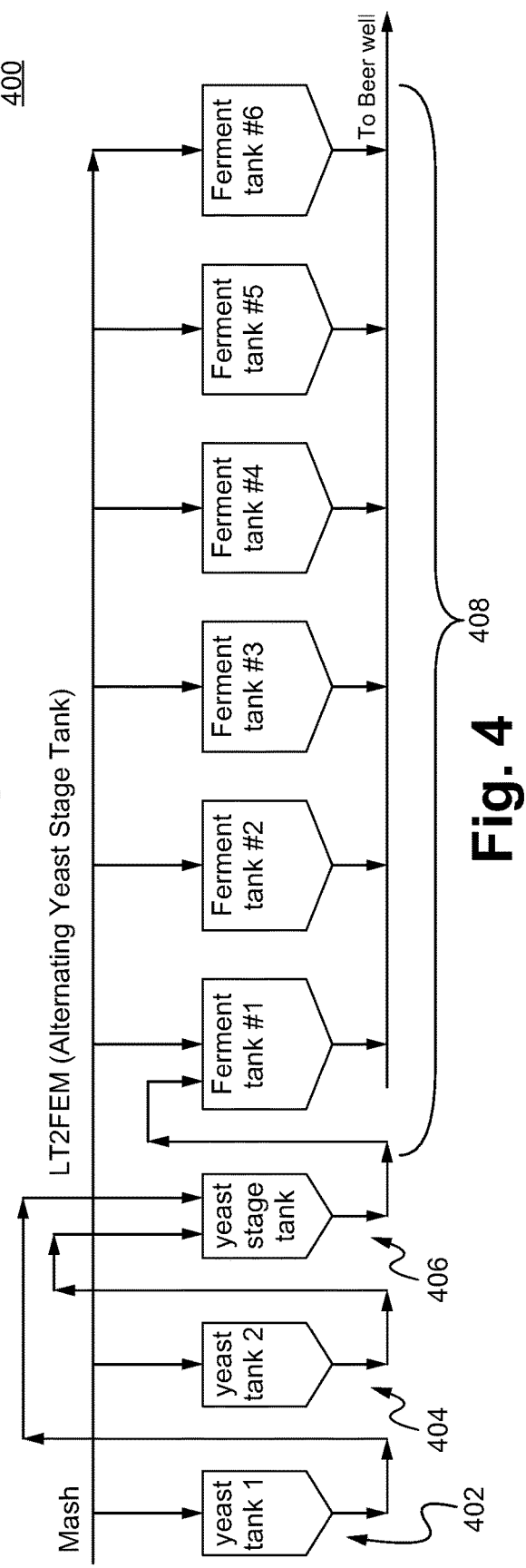

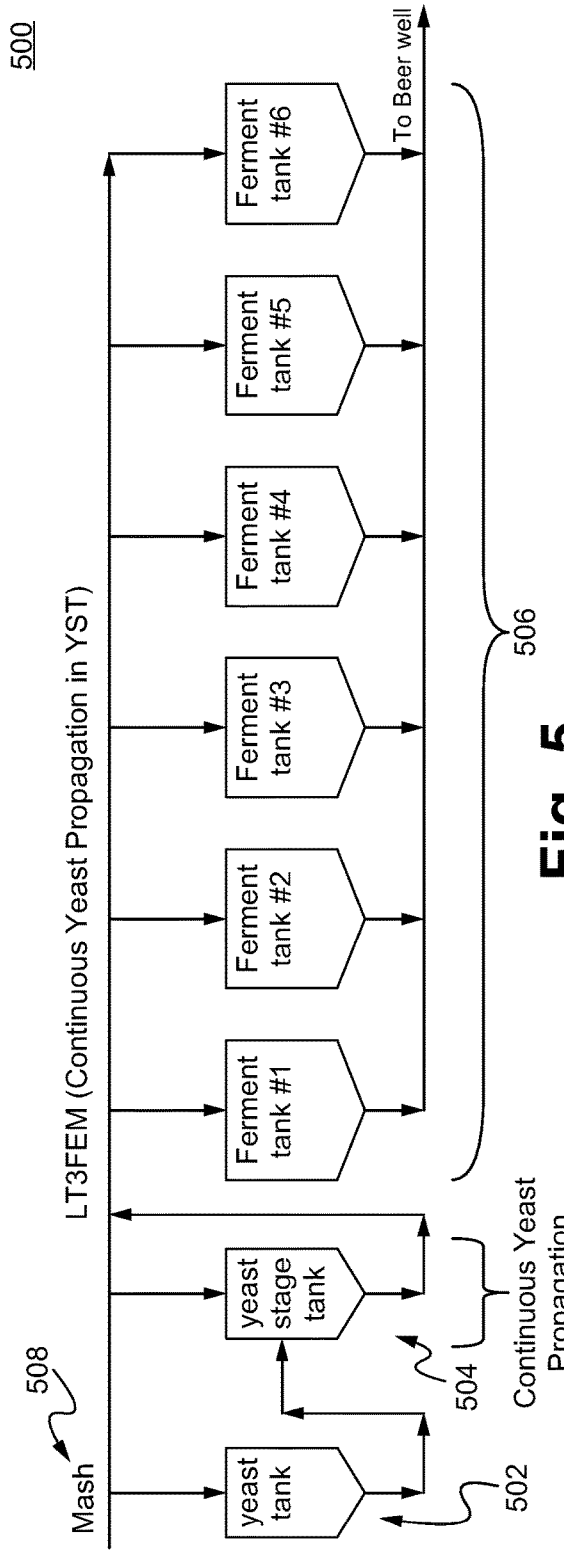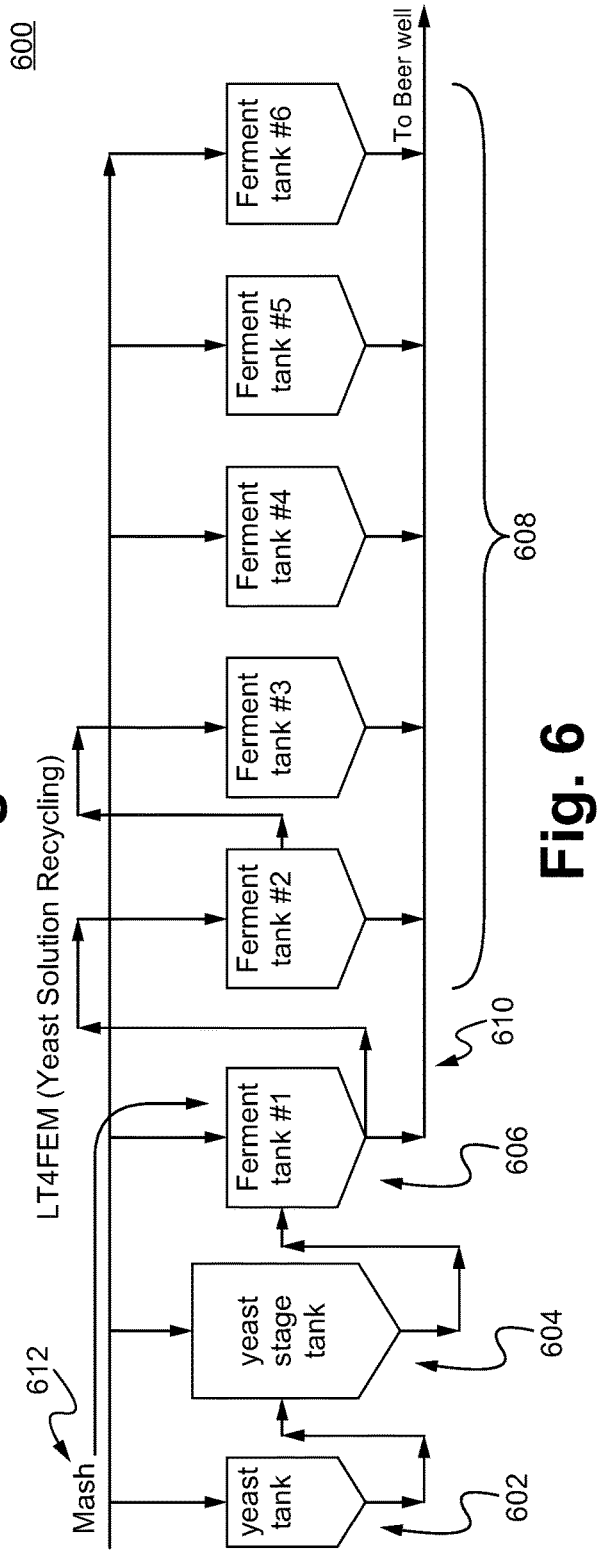

YEAST STAGE TANK INCORPORATED FERMENTATION SYSTEM AND METHOD

CROSS-REFERENCE TO RELATED APPLICATION(S)

This application is a continuation-in-part of U.S. patent application Ser. No. 14/839,763, filed Aug. 28, 2015 and titled "A FERMENTATION SYSTEM FOR DRY MILL PROCESSES," which claims priority to U.S. Provisional Patent Application Ser. No. 62/044,092, filed Aug. 29, 2014 and titled "NEW IMPROVEMENT FERMENTATION SYSTEM FOR DRY MILL PROCESS" and this application claims priority under 35 U.S.C. § 119(e) of the U.S. Provisional Patent Application Ser. No. 62/914,276, filed Oct. 11, 2019 and titled, "A YEAST STAGE TANK INCORPORATED FERMENTATION SYSTEM," which are all hereby incorporated by reference in their entirety for all purposes.

FIELD OF THE INVENTION

The present invention relates to the field of fermentation. Specifically, the present invention relates to the yeast conditions for the fermentation.

BACKGROUND OF THE INVENTION

Scientists have researched and developed the use of ethanol, a two-carbon alcohol compound, as an effective additive to gasoline to curb the rapid usage of gasoline. In some cases, gasoline mixtures have as high as 85% volume of ethanol as a biofuel. Although coal and oil produce carbon dioxide from previously long-term sequestered carbon, the carbon dioxide produced from the combustion of grain alcohol is consumed by growing the grain and quickly recycled into the environment resulting in no net carbon dioxide addition to the atmosphere, thus not leading to greenhouse gas accumulation.

In a fermentation process, ethanol and carbon dioxide are produced via a biological process, where sugar and yeast are mixed together, and the sugar is converted into cellular energy. The yeast metabolizes carbohydrates (primarily monosaccharides and disaccharides) to produce ethanol (liquid) and the byproduct carbon dioxide (gas). Under carefully moderated pH and temperature conditions to grow the yeast, the sugar-to-ethanol conversion can be up to 98% of theoretical maximum. Maximizing the yield and purity of ethanol is essential for commercial profitability.

Fermentation is an anaerobic process that is conducted in the absence of large concentrations of oxygen. The formula is simple sugar (e.g. Glucose)+yeast→$2C_2H_5OH$ (ethanol)+ $2CO_2$ (carbon dioxide). In general, there are two types of fermentation systems in ethanol-producing modern dry mill plants. One type is continuous fermentation, which is illustrated in FIG. 1. The other type is batch fermentation, which is shown in FIG. 2. The continuous fermentation as illustrated in the FIG. 1 starts in 1950s for alcohol production process for either dry mills or wet mills. Of approximately 200 dry mill plants in the U.S., about 50 plants started with this continuous fermentation system. But the majority of plants have changed to batch fermentation now, even though continuous fermentation has many advantages over a batch system.

FIG. 1 illustrates a typical continuous fermentation system 100. One or two yeast tanks 102 about half the size of fermentation tanks 104, 106, 108, 110, 112, and 114 continuously propagate yeast to supply to the fermentation tanks. In general, 6 to 12 fermenters are setup in a series and operate continually. The mash flow 116 is split into 3 parts. One part goes to a yeast tank 102 and other two go to fermenter tank #1 104 and fermenter tank #2 106. (Some plants even use a third tank: fermenter tank #3 108). The percentage of alcohol in the fermenter tank #1 is normally around 5%, with alcohol content increasing faster in the beginning and then gradually slowing by the end. The maximum percentage of alcohol in drop (after fermentation when moving to a distill tower) is normally around 12W/V (e.g., 12%/liter).

Major advantages of continuous fermentation include: a) it's a simple continuous operation; b) low yeast propagation costs; and c) low enzyme costs. The major disadvantages of continuous fermentation include: a) lower % alcohol in drop (after fermentation when moving to a distill tower, b) high % sugar in drop, c) it needs a longer time to start up; d) infections are very hard to stop, e) incomplete fermentation can happen; and f) no stable condition while in operation. The lack of control over infections is the major problem in continuous fermentation: infections can happen at any time, and if an infection occurs, the infection often wipes out all the cost savings in a very short time. This is the reason not many dry plants still use continuous fermentation in the U.S.

Instead, the majority of the 200 dry mill plants in the U.S. use the batch fermentation process, which is shown in the FIG. 2. Batch fermentation plants run a fermentation process flow of a 30-80 hour cycle (majority are in a 50-60 hour cycle) with multiple (usually between 3 and 10) fermenter tanks per facility. Yeast can be conditioned in a yeast growth tank, often called propagation tank. When the yeast in the Yeast Propagation Tank has grown to a mature, healthy state, the Yeast Solution is dumped into a Fermenter Tank. Enzyme(s) is added to the fresh mash to convert dextrin in the mash to simple sugars.

The fermenter tank is then filled with fresh mash over a period of 5 to 18 hours or until the fermenter tank is full. The fermenter tank is then set to idle, allowing the yeast to continue to ferment sugars to alcohol. At the end of the cycle, the fermentation broth is discharged and the Fermenter Tank is cleaned to be ready for another cycle. Fermentation cycles are normally 50 to 60 hours in dry mill plants in the U.S. For a 4-fermenter system, filling time is around 14 hours and the fermentation cycle is 56 hours; for a 7 fermenter tanks system, filling time is 8 hours and the fermentation cycle is 56 hours.

Over 150 dry mill plants in the U.S. operations use batch fermentation. In these plants, 100 lbs. of dry yeast are added to 2400 gallons of yeast slurry, and water plus nutrients are added to condition the yeast for propagating in the yeast tank. In the most common design, yeast tanks are normally 20,000 gallons, with one yeast tank for a 3 to 6 fermenter system, and two yeast tanks for a 7 to 10 fermenter system. The yeast propagation time ranges from 6 hours to 11 hours, depending on the number of fermenters in system. For example, for 4 fermenters, the filling time is around 14 hours, and it normally needs three hours to move the solution from the yeast tank to the fermenter tank and Clean-In-Place (CIP) for next batch. So, the yeast propagation time is 11 hours. For 7 fermenters, filling time is 8 hours, two yeast tanks are used (since with one yeast tank the yeast propagation time is too short at 5 hours), with a yeast propagation time of 15 hours. The yeast propagation rate in the yeast tank is associated with the factors including the operational conditions (temperature, pH etc.), the type of yeast used, the amount of nutrients added, and the amount of dissolved air in the yeast tank. Yeast cells will increase at a rate of about 25 to 40% per hour in the typical systems with the majority within the 30 to 35% range.

SUMMARY OF THE INVENTION

The present disclosure provides systems for and methods of providing both the yeast tank and fermenter tanks having optimized yeast cell counts at all times. More specifically, the present disclosure provides a dual-function Yeast Stage Tank (YST) (for yeast propagation and fermentation) between the yeast tank and the fermentation tank, which is illustrated in FIGS. 3-8. In some embodiments, the yeast stage tank is a separate tank that is between the yeast tank and the fermenter tank. In some other embodiments, one or more fermenter tanks are used as the yeast stage tank, which has a condition configured to perform a function as a yeast stage tank including yeast propagation such that a predetermined cell count is obtained before performing fermentation or transferring the yeast solution to a fermenter.

The yeast stage tank of some of the embodiments supplies active young yeast to the fermenter to maximize outcomes in the yeast propagation tank. In some embodiments, the yeast stage tank is also used as a yeast propagation tank for yeast propagation. Fresh mash continues to feed into the yeast stage tank and maintain an optimized yeast cell count (>250*10^6) solution from the yeast stage tank to one or more fermenter tanks during the entire filling period. The yeast stage tank is configured to supply an optimized yeast cell solution to one or more than one fermenter tanks.

In some embodiments, the yeast stage tank is used for filling up gaps of providing predetermined yeasts between the yeast tank and the fermenter tanks to ensure sure that the yeast cell count maintains maximum in fermenter tanks during the filling period when the yeast tank is too small. In some embodiments, the yeast stage tank is also used as a continue yeast propagation tank to supply a lot yeast cell to maintain a maximum yeast cell count in fermenters during the ferment filling period.

The minimum yeast stage tank size is determined by a yeast propagation rate in yeast stage tank mash rate, which is summarized in TAB 4. For example for a 20% per hour yeast growth rate (propagation rate), the size of the yeast stage tank must be larger than 5 (100/20=5) time of mash rate. For a 25% per hour yeast growth rate, the yeast stage tank must be at least 4 (100/25=4) times of mash rate. For 30% per hour yeast growth rate, the yeast stage tank must be at least 3.333 (100/30=3.333) time of mash rate. For 35% per hour yeast growth rate, the yeast stage tank must be at least 2.86 (100/35=2.86) times of mash rate. In other words, the size of the yeast stage tank can be determined using the formula of [100/% of the yeast growth] times mash rate. The average mash rate is gallon per hour (GPH) of a dry mill plant. The average mash rate is total volume of mash produce per hour for a fermentation system. So this average mash rate is equal to sum of mash rate that is sent to yeast tank, yeast stage tank and fermenter.

For a seven fermenter tanks system with fermenter size of 800,000 gal, the filling time is 8 hour with an average of mash rate of 100,000 gal per hour. If a yeast growth (propagation) rate is 20%, 25%, 30% and 35%, the yeast stage tank shall be minimum of 500,000 gal, 400,000 gal, 333,3333 gal and 285,714 gal respectively.

When larger size yeast stage tank is used, one of the fermenters can be used as a yeast stage tank first by receiving a yeast solution from the yeast tank. Next, the mash is added to a predetermined volume. Next, the fermenter tank is used as a continue yeast propagation tank (e.g., a yeast stage tank), which is used to fill up more than one fermenter tanks. This continue yeast propagation can be stopped at any time, and followed by filling up with mash until full, which is then functioned as a typical fermenter tank by continuing to finish the process of fermentation. In other words, this setup uses one of the fermenters as a yeast stage tank first. Subsequently, the yeast stage tank is used as one of the fermenter tanks later, which is able to save the costs of using a separate yeast stage tank but would decrease the total fermentation capacity.

The system provides and maintains the ideal/optimized yeast cell count solution for both the yeast tank and fermenter tank at all times. The system adds a dual function (yeast propagation and fermentation) yeast stage tank between the yeast tank and the fermentation tank. This yeast stage tank supplies huge amounts of ideal/optimized yeast cell count solution to a fermenter by a) using the yeast stage tank for continuous yeast propagation, b) recycling the ideal yeast solution from one fermenter to another fermenter, c) using both a) and b) to maintain a maximum yeast cell count (>250*10^6) in the yeast stage tank and fermenter at all times and especially during the filling period, and d) keeping the food/yeast cell ratio less than 10 (e.g., <4) at all times to avoid a) a yeast stress which produces unwanted glycerol and b) a bacterial spike which produces unwanted lactic acid. The food/yeast cell ratio is able to be represented by using the factor of % DT/% Yeast by weight ratio (or "food" to yeast ratio).

Further, the yeast stage tank is configured to stop at any time and followed by dumping the yeast solution to the fermenter tank. Such a dump would be followed by a Clean-In-Place (CIP) step and then restart of another batch in the yeast stage tank. In some embodiments, enzyme dosage is also controlled in the yeast stage tank to ensure the food/yeast cell ratio is less than 5/1 to avoid a) yeast stress caused by overproduction of glycerol and/or b) bacteria out run the yeast leading to unwanted lactic acid.

An additional benefit of the yeast stage tank is the ability to provide maximized Yeast Cell Count (YCC) solution to the appropriate fermentation tank. At any point in the process, the YST (yeast stage tank) can stop filling a fermentation tank, refill with mash, and act as a fermenter tank with a significantly shorter fermentation time as shown in FIG. 8.

As mentioned above, most of the over 200 dry milling plants in the USA use batch fermentation systems. These systems maintain 3 to 10 fermentation tanks. The average fermentation cycle time is around 56 hours. Normally, filling time for a 3 fermenter system is 18 hours; for a 4 fermenter system 14 hours; for a 5 fermenter system 11 hours; for a 6 fermenter system 9 hours, for a 7 fermenter system 8 hours, for a 8 fermenter system 7 hours, for a 9 fermenter system 6 hours, and for a 10 fermenter system 5 hours. Generally an 800,000 gallon fermenter tank uses a 20,000 gallon yeast tank. For a 20,000 gallon yeast tank to fill an 800,000 gallon fermentation tank, yeast needs to propagate 40 times during a short filling time. Under normal conditions, yeast cell count increases at around 30% per hour. Therefore, as shown in TAB 1, total time needed is 14 hours for yeast propagation time and 3 hours to transfer the yeast solution. Additionally, Clean-In-Place (CIP) time should be considered.

A majority of dry milling plants in the U.S. have more than 3 fermenter tanks in their batch fermenter system, which are operate under a much lower yeast cell count (<100*10^6/ml). This lower yeast cell count creates yeast stress and produces unwanted byproducts especially glycerol. The yeast stress also gives bacteria a chance to outcompete the yeast and produce lactic acid. A computer simulation and field data are used to set up the system to maintain maximum yeast cell count in both the yeast tank and the fermenter tank. The computer simulation is based on a yeast growth rate of 20 to 35%, and alcohol production per cell per hour is 0.001% for yeast tank and 0.002% for fermenter tank. These numbers can change during the actual operation based on observed fluctuations and other relevant variables. See TAB 1 to TAB 3 for details.

In some embodiments, a yeast stage tank (YST) is used between the yeast tank and the fermenter tank, which is a novel and nonobvious feature that has not been done before. In some embodiments, the yeast stage tank is larger than 3.33 times of an average mash tank/yeast tank, such that a yeast cell grow rate of 30% per hour is obtained, which is further confirmed by using computer simulation calculation. See TAB 4 for various yeast grow rates.

At least six different embodiments are provided below illustrating some of the selected embodiments. The embodiments illustrated below allow different typical dry mill plant configurations to improve productivity and reduce costs by maintaining a maximum yeast cell count at all times, which also provide advantages of decreasing yeast and enzyme costs, decreasing the chance of infection and shortening the fermentation cycle. See LT1FEM to LT6FEM on following:

LT1FEM (Split Flow Method): Mash flow is split to feed two fermenter tanks at the same time, which serve as yeast stage tanks in accordance with some embodiments. In some embodiments, the filling time doubles and the mash flow to the fermenter tanks is controlled in the first half of filling period to obtain maximum fermenter tank yeast cell count at all times.

TAB 5 shows current yeast tank (20,000 gal) used as a yeast tank for a 7 fermenter tanks system. TAB 6 shows an optimized yeast stage tank size (333,163 gal) used for a 7 fermenter tanks system. TAB 7 compares alcohol percentage and yeast cell count between LT1FEM (split flow method) with a minimum yeast stage tank and commonly used fermentation systems with different numbers of fermenter tanks. TAB 8 compares percentage alcohol over time on 7 fermenter tanks systems using LT1FEM method with different sized yeast stage tanks. As shown, more than one yeast stage tank in series is needed for a fermentation system with 7 or more fermenters.

LT2FEM: (Alternating YST Method) Two yeast propagation lines are set up to alternate supplying yeast solution for a fermenter via a yeast stage tank. Multiple yeast stage tanks in series are needed for more than 6 fermenter systems. This set up is ideal for switching customers from a continuous fermentation system to a batch fermentation system.

In some embodiments, two existing large yeast tanks in continuous fermentation system are used as two large yeast stage tanks in the LT2FEM system.

TAB 9 shows two large yeast stage tanks (333,163 gal) alternating supply for a 7 fermenter system with 8-hour filling time. TAB 10 shows two yeast tanks with one large yeast stage tank for a 7 fermenter system with LT2FEM set up. TAB 11 shows two yeast tanks plus two large yeast stage tanks are needed for a 10 fermenter system with LT2FEM system set up. TAB 12 compares alcohol percentage over time between the LT2FEM system and currently used fermentation systems. TAB 13 is a summary of yeast tank sizes and yeast stage tank sizes needed for various fermentation systems.

LT3FEM: (Continuous Yeast Propagation in YST Method) A yeast stage tank (YST) is used between the yeast tank and the fermenter tank. The yeast stage tank is used as a continuous yeast propagation tank by continuing feeding mash in and continuing to send yeast solution out to the fermenter. This method fills up the fermenter tank without using any new yeast solution from the yeast tank. Thus, yeast propagation can continue for more than one fermenter. When this continuous yeast propagation is used for one fermenter, the yeast propagation time in the yeast tank and the yeast stage tank are double. When continuous yeast propagation is used for two fermenters, the time needed in the yeast tank and the yeast stage tank are triple. This decreases the capital cost and operational cost of yeast propagation. TAB 14 shows yeast stage tank used as a continuous yeast propagation tank for one pass (yeast solution is passed from one tank to the next) (to provide solution for only one fermenter tank) for a 7 fermenter LT3FEM system. TAB 15 shows a yeast stage tank used as a continuous yeast propagation tank for one pass (to provide solution for only one fermenter tank) for a 10 fermenter LT3FEM system. TAB 16 compares alcohol percentage over time between the LT3FEM system and various currently used fermentation systems. TAB 17 shows the yeast tank size and yeast stage tank size needed for LTFEM3 system.

LT4FEM: (Yeast Solution Recycling Method) A larger yeast stage tank is added between the yeast tank and the fermenter tank. This yeast stage tank is used to produce a larger amount of the most active young yeast cells to the fermenter. This huge amount of active young yeast is dumped to fermenter #1 (donator fermenter tank) followed by adding mash to fermenter #1 until full. The yeast stage tank used is large enough to make sure the yeast cell count in fermenter tank #1 maintains maximum yeast cell count ($>250*10\textasciicircum6$) during the filling period. The computer simulation program further shows the yeast stage tank needs to be at least 3.33 times the mash rate for a 30% yeast propagation rate. The minimum yeast stage tank sizes for different yeast growth rates are shown in TAB 4. Once fermenter #1 (donator fermenter) is full, it will continue to propagate yeast (acting as a yeast stage tank) for at least three hours by continuing to bring more mash in and sending ideal yeast solution out to fermenter tank #2 (receptor fermenter). This at least three-hour yeast solution transfer from fermenter tank #1 (donator fermenter) to fermenter tank #2 (receptor fermenter) ensures that fermenter tank #2 will always have maximum yeast cell count ($>250*10\textasciicircum6$) during the filling period. Next, fermenter tank #2 can start acting as a yeast stage tank by filling with mash until full. Once fermenter #2 is full it can continue to intake mash while sending maximum yeast cell count solution to another fermenter. This method can be continuously applied to each new fermenter maintaining an ideal yeast count during fill and then, once full, in-taking more mash while donating ideal yeast count solution to the next fermenter. This method allows a recycling of the ideal yeast cell solution, ensures ideal yeast cell counts are maintained at all times in each fermenter, and requires significantly less enzyme. Thus, both operational and capital costs can be reduced. TAB 18 shows a 7 fermenter system with a yeast stage tank and one yeast recycle pass (yeast solution passed from one fermenter to another). TAB 19 shows a 10 Fermenter system with a yeast stage tank and one yeast recycle pass. TAB 20 compares the alcohol percentage over time between the LT4FEM system and currently used 7 and 10 fermenter systems. TAB 21 shows the size of the yeast tank and yeast stage tank needed for a LT4FEM system.

LT5FEM: (Continuous Yeast Propagation in YST or Fermenter Method) This system combines the continuous propagation of active yeast solution in a yeast stage tank used in LT1, LT2, and LT3 methods with the recycling method of LT4FEM. LTSFEM uses a yeast stage tank to provide huge quantities of active young yeast cells to more than one fermenter by using a yeast stage tank as a continuous yeast propagating tank (LT3FEM) or using a fermenter as a continuous yeast propagation tank (LT4FEM). With this system, there are many ways to set up an optimum yeast propagation system for batch fermentation. TAB 22 shows the minimum size of a yeast stage tank needed for various systems. TAB 23 shows a simulation for a 7 fermenter system using one yeast stage tank for continuous yeast propagation and using a minimum size yeast stage tank for one yeast recycle pass (yeast solution passed from one fermenter to another). TAB 24 shows a simulation for a 7 fermenter system using one yeast stage tank for continuous yeast propagation and using a maximum size yeast stage tank for one yeast recycle pass. TAB 25 shows a simulation for a 10 fermenter system using one yeast stage tank for continuous yeast propagation and another for yeast recycle pass with LTSFEM system. TAB 26 shows a simulation for a 10-fermenter system using two yeast stage tanks for yeast recycling. TAB 27 shows a simulation of a 10 fermenter system using two yeast stage tanks for continuous yeast propagation.

LT6FEM: (Fermenter Tank used as YST Method) The above systems (LT1FEM, LT2FEM, LT3FEM, LT4FEM, and LTSFEM system) need to a) add an additional yeast stage tank to the existing system, b) dump yeast solution to fermenter, and c) Clean-in-Place (CIP) the yeast stage tank. These needs add capital cost and operational cost. LT6FEM system is developed by using one fermenter as a yeast stage tank. This yeast stage tank can continuously propagate yeast by adding mash to the tank while sending maximized yeast cell count solution to a fermenter. This yeast stage tank, which is continuously propagating yeast, can fill multiple fermenters with ideal yeast cell count solution. At any time this tank can stop yeast propagation and act as an additional fermenter by filling with mash and stopping donation of yeast solution to another fermenter. During this time, another fermenter tank can begin acting as a yeast stage tank. This way, the first yeast stage tank fills up with mash to become a fermenter and the next fermenter starts acting as a yeast stage tank. Using this strategy all yeast stage tanks and fermenters consistently maintain maximum yeast cell counts (>250*10^6) during the filling period. Thus, the alcohol percentage (which starts around 2%) will gradually increase and not create any sudden alcohol percentage changes when the yeast solution is passed from one fermenter to another (recycle pass) as seen in the LT4FEM system. Using this continue yeast propagate in yeast stage tank technique, the LT6FEM system will increase alcohol percentage from 2% up to 6% during the filling period and reach a maximum of 0.5% per hour rate. Thus, LT6FEM can operate on a 48-hour (two days cycle) fermentation cycle instead of the currently used 56-hour fermentation cycle. TAB 28 shows LT6FEM using one recycling pass with each fermenter in the system taking turns acting as a yeast stage tank (propagating yeast and feeding next fermenter) for a 4 fermenter system with a 16-hour filling time. TAB 29 shows summary of the LT6FEM system with various fermentation systems. TAB 30 show a summary of alcohol percentage in fermenter using LT6FEM system. TAB 31 shows the minimum size of a yeast tank needed for a LT6FEM system. TAB 32 shows the minimum size of a yeast stage tank needed for a LT6FEM system. TAB 33 shows the average alcohol percentage at hour 18 with a minimum size yeast tank. TAB 34 shows the decrease in fermentation time with a minimum size yeast tank. TAB 35 shows the pounds of dry yeast needed with a minimum size yeast tank. TAB 36 compares yeast cell count and alcohol percentage between currently used systems and an LT6FEM system for a 7 fermenter system. TAB 37 shows a summary of alcohol percentage after 18 hours after multiple recycling passes (fermenter to fermenter yeast solution transfer) using the LT6FEM method for a 7 fermenter system.

Use of a larger yeast stage tank provides more stable operation (allows lower yeast growth rate and a shorter fermentation cycle). But a larger yeast stage tank requires more spaces to accommodate the larger yeast tank. For all batch systems, the maximum size yeast stage tank operation capacity will be the same as the fermenter capacity. TAB 38 shows the size of yeast tanks needed for various yeast growth rates with a maximum size yeast stage tank in a LT6FEM system. TAB 39 shows the average alcohol percentage at hour 18 for various yeast growth rates with maximum size yeast stage tank on LT6FEM system. TAB 40 shows the decrease in fermentation time due to the use of a maximum size yeast stage tank for various yeast growth rates on LT6FEM system. TAB 41 shows the amount of dry yeast needed for a maximum size yeast stage tank with various yeast growth rates on LT6FEM system. A comparison of minimum size yeast stage tank data (TAB 31 to TAB 35) with maximum size yeast stage tank data (TAB 38 to TAB 41) shows that there are many different ways for a customer to improve operational conditions and decrease costs by using LT6FEM technology to optimize their fermentation system.

This computer simulation program also can be used to aid the design of new fermentation systems. All of the computer simulation data shows that systems with fewer fermenter numbers (4 to 6) and longer filling times (9 to 16 hour) cost less and perform better than fermentation systems with more fermenters (7 to 10) and shorter filling times (5 to 8 hour). The computer simulation data demonstrates that existing larger number (7 to 10) fermentation systems can be turned into two better performing fermentation systems. For example, a 8 fermenter system with 7 hour filling time can be made into two 4 fermenter systems with 14 hour filling times. Similarly, a 10 fermenter system with 5.5 hour filling time can be made into two five fermenter systems with filling times of 11 hours as shown in TAB 30.

The computer simulation program is a very useful and valuable tool for designing new fermentation systems and for improving current system operation. The simulation can a) analyze the field data, b) find the location of abnormal operation or inefficiency, c) model various modifications to the system, and d) compare different fermentation modifications. This allows new fermentation systems to be optimally designed and existing systems to be optimized for cost and performance. Generally, one small mistake in actual field operation can lead to a huge loss in profit. In addition, a single day of computer simulation can provide more useful data than hiring a fermentation specialist to collect data in the field for decades.

In the following, some experimental data are provided in accordance with some embodiments. TAB 1 shows some important yeast propagation methods and data. The right yeast tank has been designed depending on the yeast propagation time in the system. Plot 1-1 shows the yeast cell increase ratio as a function of yeast propagation with various yeast propagation rates (from 0.25 to 0.4). The yeast propagation time has been used to design an ideal yeast tank propagation system. The percentage of alcohol in the yeast tank versus time is also plotted in Plot 1-2 using a computer simulation with various alcohol production rates (0.001% to 0.0015% alcohol produced per yeast cell per hour). This number depends on the type of yeast, yeast tank conditions (pH temperature and nutrient etc.) and most importantly, the dissolved air inside the yeast tank. Normally, plants only have yeast propagation data at the end of yeast propagation. However, those two plots are very useful for understanding and designing a yeast propagation system that considers limiting factors, how to improve results, and what to expect with all possible improvement options. These two plots are able to be used to guide design and the operation of the yeast tank to maximize yeast cell count with the most active (high % budding and viability) young yeast for the fermenter tanks.

A computer simulation program shown in TAB 2 (for a current 7-fermenter system) is based on 100 lbs. of dry yeast in a 2400 gallon yeast slurry tank, then transferred to a 20,000 gallon yeast tank for a 16 hour yeast propagation cycle in the yeast tank to produce 20,000 gallons of active young yeast which are then transferred to a 800,000 gallon fermenter tank. With a mash rate of 100,000 gallons per hour, the fermenter tank will take 8 hours to fill up. As shown in TAB 2, the yeast cell count remains very low during this 8-hour filling period, as it takes 14 hours to reach the maximum yeast cell count. Similarly, the data shows a 15-hour lag period for alcohol production. The glucose in the fermenter tank also gradually increases from about 1% to as high as 14% during this period. This high glucose and low yeast cell count period creates yeast stress and produces the unwanted byproduct glycerol. The data shows that the percentage of glycerol increases from around 0.5% to as high as over 1% during this period with regular dry yeast. Some recently released GMO yeasts can decrease the percentage of glycerol to less than 1% and increase alcohol yields up to 2.5%.

The same computer simulation program is used for 4 to 10 fermenters in the current fermentation systems and is summarized in TAB 3. Yeast Cell Counts (YCC) in the fermenters start very low ($93*10^6$ for a 4 fermenter system, $76*10^6$ for a 5 fermenter system, $39*10^6$ for a 6 fermenter system, $54*10^6$ for a 7 fermenter system, $48*10^6$ for a 8 fermenter system, $42*10^6$ for a 9 fermenter system and $27*10^6$ for a 10 fermenter system), so the yeast in the fermenter is under stress during and after the filling time: 14 hours for a 4 fermenter system, 15 hours for a 5 fermenter system, 16 hours for a 6 fermenter system, 15 hours for a 7, 8 and 9 fermenter system, and 16 hours for a 10 fermenter system. In contrast, a typical system spends more than 14 hours with a low yeast cell count (less than $250*10^6$). The low yeast cell count stresses the yeast causing glycerol production, which slows the alcohol production rate for more than 14 hours.

Normally, improving this fermentation system requires a big capital investment, additional operational costs, and longer development time. This computer simulation program provides a much quicker, less expensive, and easier way to develop new fermentation technology, since many possible improvements can be tried in the computer simulation program and results compared prior to adjusting the system.

As described in the provisional Patent Application Ser. No. 62/044,092, filed Aug. 29, 2014 and titled, "NEW IMPROVEMENT FERMENTATION SYSTEM FOR DRY MILL PROCESS," recycling yeast from a donating fermenter to a receiving fermenter can keep the yeast cell count at a maximum ($>250*10^6$) for all receiving fermenters, and produce less glycerol (as low as 1.1%) are all incorporated by references for all purposes. However, the yeast cell count in the donating fermenter is still very low and the percent of glycerol in the donating fermenter may be as high as 1.5%.

In addition, a measurable and useful parameter, % DT/% Yeast by weight ratio (or "food" to yeast ratio), is also introduced. (e.g., % DT=glucose) This ratio offers information on the health status of the yeast after every hour and a method of smoothly transferring the yeast from yeast-growing phase to alcohol producing phase during a fermenter filling period, such that shocks to the yeast are able to be avoided. Because the yeast cell count in the donating fermenter is still very low, bacteria has time to get a foothold in the donating fermenter and to be transferred to the receiving fermenter, creating a chance that bacteria outruns yeast in the donating fermenter.

BRIEF DESCRIPTION OF THE DRAWINGS

Embodiments will now be described by way of examples, with reference to the accompanying drawings which are meant to be exemplary and not limiting. For all figures mentioned herein, like numbered elements refer to like elements throughout.

FIG. 1 illustrates a typical continuous fermentation system.

FIG. 2 illustrates a typical batch fermentation system.

FIG. 3 illustrates a mash split flow process in accordance with some embodiments.

FIG. 4 illustrates alternating yeast tanks as a yeast stage tank process in accordance with some embodiments.

FIG. 5 illustrates a continuous yeast propagation in a YST in accordance with some embodiments.

FIG. 6 illustrates a yeast solution recycling process in accordance with some embodiments.

DETAILED DESCRIPTION OF THE PREFERRED EMBODIMENT

Figure 7:
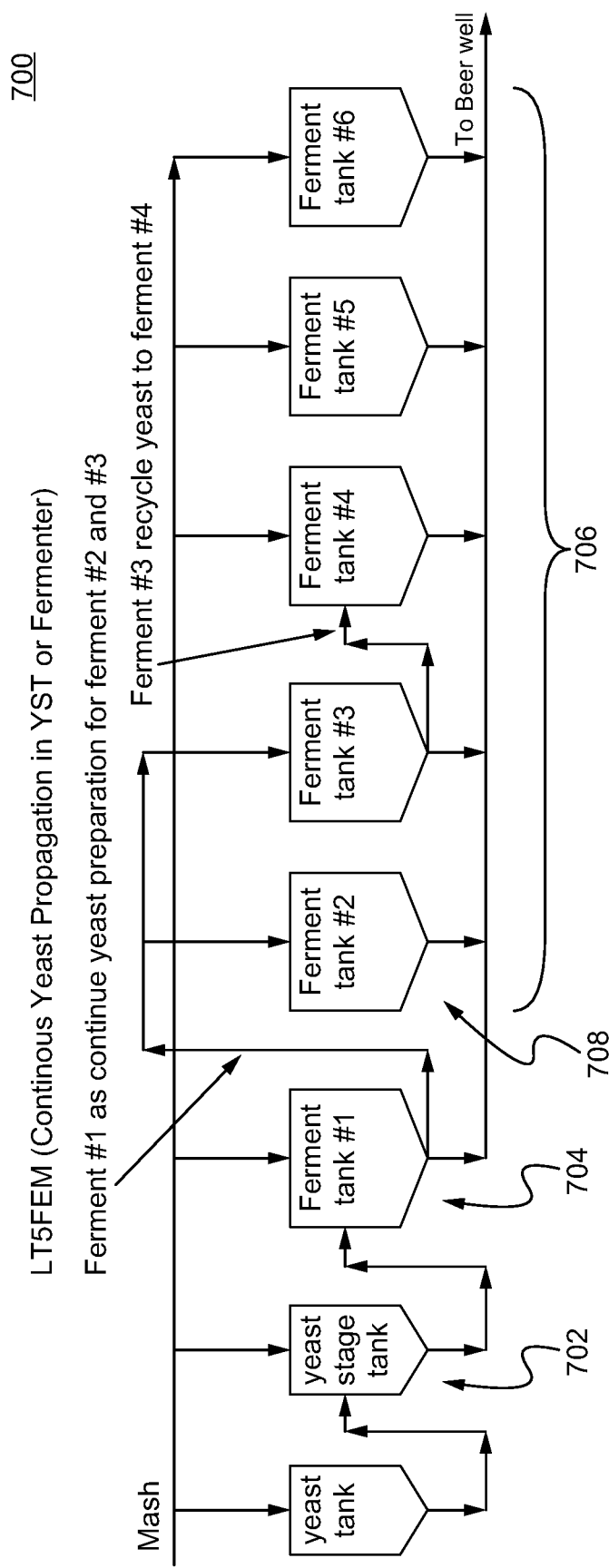
FIG. 7 illustrates a continuous yeast propagation in YST or a fermenter tank in accordance with some embodiments.

Reference is made in detail to the embodiments of the present invention, examples of which are illustrated in the accompanying drawings. While the invention is described in conjunction with the embodiments below, it is understood that they are not intended to limit the invention to these embodiments and examples. On the contrary, the invention is intended to cover alternatives, modifications and equivalents, which can be included within the spirit and scope of the invention as defined by the appended claims. Furthermore, in the following detailed description of the present invention, numerous specific details are set forth in order to more fully illustrate the present invention. However, it is apparent to one of ordinary skill in the prior art having the benefit of this disclosure that the present invention can be practiced without these specific details. In other instances, well-known methods and procedures, components and processes have not been described in detail so as not to unnecessarily obscure aspects of the present invention. It is, of course, appreciated that in the development of any such actual implementation, numerous implementation-specific decisions must be made in order to achieve the developer's specific goals, such as compliance with application and business-related constraints, and that these specific goals vary from one implementation to another and from one developer to another. Moreover, it is appreciated that such a development effort can be complex and time-consuming but is nevertheless a routine undertaking of engineering for those of ordinary skill in the art having the benefit of this disclosure.

The present invention has been described in terms of specific embodiments incorporating details to facilitate the understanding of principles of construction and operation of the invention. Such reference herein to specific embodiments and details thereof is not intended to limit the scope of the claims appended hereto. It is readily apparent to one skilled in the art that other various modifications can be made in the embodiment chosen for illustration without departing from the spirit and scope of the invention as defined by the claims.

LIST OF TABLES OF COMPUTER SIMULATION DATA

TAB 1: Batch method yeast propagation theory and data.
TAB 2: Computer simulation for a current ICM 7 fermenter system with two 20,000 gallon yeast tanks.
TAB 3: Summary of results on all current ICM batch fermentation systems (from a 4 fermenter system to a 10 fermenter system) by computer simulation.
TAB 4: Shows minimum yeast stage tank size required to maintain maximum yeast cell count.
TAB 5: Computer simulation for a 7 fermenter system with LT1FEM (split mash flow method).
TAB 6: Computer simulation showing optimum (maximum) yeast stage tank size (333,163 gallon) for a 7 fermenter system with LT1FEM.
TAB 7: Compares results between current ICM systems and LT1FEM system.
TAB 8: Compares alcohol percentage over time for a 7 fermenter system with various yeast stage tank sizes with LT1FEM setup.
TAB 9: Computer simulation for a 7 fermenter system with LT2FEM system.
TAB 10: Other set up for a 7 fermenter system with LT2FEM system.
TAB 11: Computer simulation for a 10 fermenter system with LT2FEM system.
TAB 12: Compares results between LT2FEM system and current ICM systems.
TAB 13: Shows yeast stage tank size, yeast tank size, and dry yeast need for LT2FEM system.
TAB 14: Computer simulation for 7 fermenters with LT3FEM system.
TAB 15: Computer simulation for 10 fermenters with LT3FEM system.
TAB 16: Compares results between LT3FEM and current ICM systems.
TAB 17: Shows yeast stage tank size, yeast tank size and amount of dry yeast needed for LT3FEM system.
TAB 18: Computer simulation for a 7 fermenter system with LT4FEM system.
TAB 19: Computer simulation for a 10 fermenter system with LT4FEM system.
TAB 20: Compares alcohol percentage over time between LT3FEM, LT4FEM and current ICM setup for 7 and 10 fermenter systems.
TAB 21: Shows amount of dry yeast, yeast tank size, and yeast stage tank for LT4FEM system with various number of fermenters.
TAB 22: Summary of minimum yeast stage tank size need for LT2FEM, LT3FEM and LT4FEM systems.
TAB 23: Computer simulation for a 7 fermenter system with one yeast stage tank as continuous yeast propagation tank and one yeast recycle pass with minimum size yeast stage tank.
TAB 24: Computer simulation for a 7 fermenter system with one yeast stage tank as continuous yeast propagation tank and one yeast recycle pass with maximum size yeast stage tank (same size as fermenter).
TAB 25: Computer simulation for a 10 fermenter system with one pass of continuous mash intake and continuous yeast propagation to fermenter and one yeast recycle pass setup.
TAB 26: Computer simulation for a 10 fermenter system with two recycle passes setup.
TAB 27: Computer simulation for a 10 fermenter system with two continuous yeast propagation passes (yeast solution transfers from yeast stage tank to fermenter).
TAB 28: Computer simulation program for a LT6FEM system.
TAB 28A: Compares alcohol percentage over time between LT6FEM and currently used 4 fermenter systems.
TAB 29: Summary of LT6FEM results for use of one fermenter as Yeast Stage Tank and then fermentation operation.
TAB 30: Alcohol percentage in fermenters over time at the 18 hour mark with a minimum yeast stage tank size for a LT6FEM system.
TAB 31: Yeast tank capacity needed for a minimum yeast stage tank size for a LT6FEM system.
TAB 32: Minimum yeast stage tank capacity needed.
TAB 33: Average % Alcohol at hour 18 with a minimum yeast stage tank size.
TAB 34: Decrease in fermentation time with a minimum yeast tank size.
TAB 35: Pounds of dry yeast needed with a minimum yeast stage tank size.
TAB 36: Summary of alcohol percentage for a 7 fermenter system with an LT6FEM system.
TAB 37: Summary of results for a 7 fermenter system with multiple passes using the LT6FEM System.
TAB 38: Summary for yeast tank/mash rate needed for a maximum yeast stage tank.
TAB 39: Average alcohol percentage at hour 18 mark for a maximum yeast stage tank.
TAB 40: Decrease in fermentation time with a maximum yeast stage tank.
TAB 41: Pounds of dry yeast needed for a maximum yeast stage tank.
TAB 42: Optimum fermentation design system.

For a small tank, 100 pounds of dry yeast are used in a yeast slurry tank, which fills with 2400 gallons of water to form a yeast solution with a yeast cell count of $250*10^6$. To maintain this ideal yeast count for an 800,000 gallon fermenter tank, the quantity of yeast should increase by 333 times. When a 20,000 gallon yeast tank is used, the initial 100 pounds of yeast is multiplied 8.3 times to fill the yeast tank with the optimized yeast cell count solution. Then the 20,000 gallons of yeast solution should multiply another 40 times to fill the fermenter. Current batch fermenter systems including ICM's have too small a yeast tank, which increases yeast propagation time and lengthens the fermentation cycle.

Larger yeast tanks also need more time for yeast propagation before sending the yeast solution to a fermenter. For one yeast tank systems, the yeast tank only has one filling time to propagate the yeast. Two yeast tank systems can create twice as much yeast solution in the yeast tanks thus cutting in half the time to fill fermenters. This is why larger scale fermenter systems (7 or more fermenters) use two yeast tanks. For example, 10 fermenter systems, the filling time needs only 5 hours. Two yeast tank systems will give 10-hours of yeast propagation time. Accounting for three hours of moving the solution to the fermenter and Clean-In-Place (CIP) time, the yeast propagation time only is left with 7 hours, in which time the yeast can only grow 6.27 times with a yeast growth rate of 30% per hour. Therefore, multiple yeast tanks in series are needed for 9 or more fermenter systems.

Fermentation is a complex system with living organisms. The final results always differ even when systems and operations appear identical. However, the computer simulation, in accordance with some embodiments, are used to analyze the problems, model numerous setup systems, and compare the results. Based on these results, any batch fermentation system can be optimized. The computer simulation used in this disclosure is based on following principles:

a) Yeast propagation rate per hour: Using field data as a basis, the yeast propagation rate per hour depends on the type of yeast used, yeast tank conditions (pH, temperature, etc.), the nutrients inside the yeast tank, and the amount of dissolved air in the yeast tank. The normal dissolved air levels range from 25 to 40% with most in the 30% range. Thus, 30% dissolved air is used in the computer application.

b) The alcohol production rate per hour: Using field data as a basis, the alcohol production rate in the yeast tank and fermenter tank are a function of yeast type, yeast tank and fermenter tank conditions (pH, temperature, etc.), nutrients in the yeast and fermenter tanks, and the amount of air in the yeast tank. The normal range of alcohol production is between 0.001% and 0.0015% alcohol per yeast cell per hour for the yeast tank and 0.002% alcohol per yeast cell per hour for the fermenter. Thus, 0.001% for the yeast tank and 0.002% for the fermenter tank are used as baselines in this disclosure. However, this variable can be adjusted in the computer program and can be used to better optimize fermentation systems.

c) The optimized/targeted yeast cell count in the field varies from 250 to $350*10^6$/ml. For purposes of this disclosure, an ideal yeast cell count of $250*10^6$ is used.

In some embodiments, a computer simulation is used based on the above principles/assumptions for 7 fermenter systems currently used by ICM systems as shown in TAB 2. The cell A2:U3 shows all the input data for subsequent calculations. All the numbers in red font can be adjusted based on existing system parameters or desired outcomes. The yeast tanks (A and B) calculations are shown in cell B4: K24. The fermentation calculation for fermentation tanks 1 and 2 are shown in cell L4:U24. The number projected by the computer simulation for both yeast cell count and alcohol percentage in the yeast tank and fermenter tank are extremely consistent with field data. Plot 2-1 and plot 2-2 show the yeast cell count in fermenter tanks below 60, and an alcohol percentage in fermenter tanks below 0.5% during the filling period (less than 8 hours).

Under these conditions (low yeast cell count and low alcohol percentage, there is a chance for either yeast to become stressed and produce unwanted byproducts (glycerol) or for bacteria to outgrow the yeast and produce unwanted byproducts (lactic acid). The data confirms a sharp increase in both the bacterial count and percentage of glycerol in the fermenter during the first 20 hours. The plot shows that maximum YCC (yeast cell count) $250*10^6$ is not reached until hour 14. This means that there are 14 hours of lag time before alcohol production rates are ideal.

Using the same methodology, computer simulations are also used for other batch fermenter systems (4 to 10 fermenter systems). The YCC over time and the alcohol percentage over time are shown in TAB 3. This clearly shows that yeast cell counts in all of these systems are low during the filling period. YCC reaches a maximum ($250*10^6$) at hour 14 for 4 and 5 fermenter systems, at hour 15 for 7, 8 and 9 fermenter systems, and hour 16 for 6 and 10 fermenter systems. The computer simulation data is consistent with field data. The alcohol percentage in these fermenters is all well below 1.5% during filling and lead to an alcohol production lag time of 14 to 16 hours. Ideal alcohol production is not reached until the yeast cell count reaches a maximum ($>250*10^6$), which takes between 14 to 16 hours as shown.

In some embodiments, a computer simulation program is used to perform and/or optimize fermentation systems to maintain a maximum YCC in both yeast tanks and fermenter tanks. When a maximum YCC is maintained during and after the filling period, bacterial growth and yeast stress can be avoided. In addition, alcohol production has a significantly shorter lag time. Following are some of the methods used:

FIG. 3 illustrates a mash split flow method 300 in accordance with some embodiments. In some embodiments, the method 300 splits the mash to feed two fermenter tanks. In some embodiments, two 20,000 gallon yeast tanks work in parallel to dump more than 35,500 gallons of propagated yeast to the fermenter every 8 hours, such that the yeast cell count in the fermenter remains ideal/optimized. In some embodiments, two yeast tanks of more than 35,500 gallons (e.g., larger yeast tanks) are installed, which are able to be operated on a 16-hour yeast propagation cycle. In some embodiments, the larger yeast tank has a size greater than 30,000 gallon yeast tank.

LT1FEM: (Split Flow Method) Using this method, mash flow 302 is split to feed two fermenters 306 and 308. The first fermenter 306 is filled to maintain a maximum yeast cell count as shown in TAB 5 for a 7 fermenter system with a 20,000 gallon yeast tank. Fermenter tanks 310 are tanks #3 to #6 that are used for performing fermentation processes.

In some embodiments, two yeast tanks (A&B) with 16-hour yeast propagation cycles can supply yeast solution to a fermenter every 8 hour. The mash rate to fermenter #1 306 is shown in cell I7:I22. The alcohol percentage in fermenter #1 306 is shown in cell K7: K22, and the YCC in fermenter #1 is shown in cell J7: J22.

The YCC (yeast cell count) in the fermenter is below maximum until hour 9 to 11, because the yeast tank is too small. In some embodiments, two 20,000 gallon yeast tanks work in parallel to dump more than 35,500 gallons of propagated yeast to the fermenter every 8 hours, the yeast cell count in the fermenter remains ideal. This two yeast tank method needs 200 pounds of dry yeast every 8 hours. To cut down dry yeast costs, two yeast tanks with more than 35,500 gallons can be installed and can operate on a 16-hour yeast propagation cycle. TAB 6 shows this by changing the 19,990 gallons in cell L6 to 39,980 gallons. With the new larger yeast tanks, only 49 pounds of dry yeast is needed every 8 hours. TAB 6 shows the optimum yeast tank size for 7 fermenter systems using the LT1FEM setup. TAB 7 compares LT1FEM and typical ICM systems with regard to YCC over time and alcohol percentage over time. LT1FEM (split flow method) can maintain a maximum YCC in the fermenter if the yeast tank has the optimum size. The ideal yeast tank size for fermentation systems with different numbers of fermenters is shown in cell B35:H35 in TAB 7. TAB 8 shows alcohol percentage over time for 7 fermenter systems with various yeast tank sizes. Advantageously, using two larger yeast tanks can decrease lag time for alcohol production and also use less dry yeast than smaller tanks. Typical ICM fermentation systems with 4, 5, 6 and 7 fermenters with 20,000 gallon yeast tanks are ideal for using the LT1FEM method. To modify, these systems just need to add control valves for the mash flow to the fermenters. For fermenter systems with 8 or more fermenters, other solutions (LT3FEM, LT4FEM or LTSFEM) are detailed later.

FIG. 4 illustrates a method 400 having alternating two or more yeast tank system in accordance with some embodiments. In some embodiments, there are two yeast propagation lines from a tank with dry yeasts to send a yeast solution to fermenters, which can be having two yeast tanks follow by one yeast stage tank. Alternatively, one yeast tank followed by two yeast stage tanks or two yeast tanks followed by two yeast stage tanks are other alternatively embodiments.

The numbers of yeast tanks and/or yeast stage tanks are able to be determined by the numbers of fermenter tanks and system operational conditions.

In some embodiments, the two-line yeast propagation system has one line sending the yeast solution to one or more of the fermenter tanks, and the other line starts to prepare new yeast solution for the next cycle of fermentation. This two-lines setup is able to operate alternately to supply a yeast solution to the fermenter tanks.

LT2FEM: (Alternating YST Method) This method 400 uses either two large yeast stage tanks (333,163 gallons) or two yeast tanks 402 and 404 (78,748 gallon) and one yeast stage tank 406 (292,384 gallon) to propagate yeast and feed yeast solution to fermenters 408. TAB 9 shows simulation data for a 7 fermenter system using LT2FEM system/technology with two large yeast stage tanks. Two large yeast stage tanks (333,163 gallons) each with a 16 hour cycle alternate providing yeast solution to a fermenter. Thus, the fermenter receives solution every 8 hours and can maintain a maximum YCC (>250*10^6) during the filling period, see cell J7:J14. Using this method, 458 pounds of dry yeast are needed every 8 hours. TAB 10 shows simulation data for a 7 fermenter system with two yeast tanks (78,748 gallon) and one large yeast stage tank (292,384 gallon).

With this solution, enough yeast is propagated to maintain a maximum yeast cell count (>250*10^6) in a fermenter during the filling period. 106 pounds of dry yeast is added to 2600 gallons of water in the yeast slurry tank, then this wet/reactive yeast with a maximum YCC is sent to a 78,748 gallon yeast tank (yeast tank A or B). The mash is gradually added to the yeast tank by controlling valves as shown in cell C13: C25 to ensure ideal YCC in the yeast tank.

Using a 16 hour yeast propagation cycle, at hour 13, the 78,748 gallons of active young yeast are sent to the yeast stage tank (292,384 gallons) to continue yeast propagation. The two yeast tanks (402 and 404) are operated on 13-hour yeast propagation time. Mash is gradually added and solution is sent to the yeast stage tank 406 at hour 13 and followed by Clean-In-Place (CIP) of the 78,748 gallon yeast tank 406. It takes 3 hours to send the yeast solution and CIP the yeast tank. Thus, yeast tanks 402 and 404 have a 16 hour yeast propagation cycle. The yeast tanks 402 and 404 alternately send yeast solution to the yeast stage tank 406, so the yeast stage tank 406 receives yeast solution every 8 hours. The yeast stage tank has a 8 hour yeast propagation cycle (5 hours to propagate yeast and 3 hours to send yeast solution to the fermenter and perform CIP). Thus, every 8 hours, the yeast stage tank receives yeast solution from yeast tanks 402 or 404 (alternating).

Mash is added to the yeast stage tank by using controlling valves (see cell I10:I14) to maintain maximum yeast cell count in the yeast stage tank 406 at all times. After 5 hours of yeast propagation in the yeast stage tank 406, the 292,384 gallons of active young yeast in solution are sent to a fermenter tank 408. This happens every 8 hours as the yeast stage tank needs 5 hours of propagation time and 3 hours to dump and CIP. After receiving 292,384 gallons of active young yeast solution, the fermenter 408 continues to add mash at an average mash rate of 100,000 gallons per hour. Cell L7:L14 shows the fermenter status after 8 hours. The YCC in the fermenter tank (see cell M7: M14) is always at a maximum (>250*10^6). The alcohol percentage in the fermenter is shown in cell N7:N14. Compared with currently used ICM fermentation systems, Advantageously, the LT2FEM can decrease the fermentation cycle by about 8 hours. Thus, by using LT2FEM technology, a fermenter system can complete a full fermentation cycle in 48 hours instead of 56 hours, which increases system efficiency by over 14 percent and is simpler for an operator to control.

As explained, the LT2FEM system uses either two yeast stage tanks (333,163 gallons) (See TAB 9) or two yeast tanks (78,748 gallons) with one larger yeast stage tank (292,384 gallons) (See TAB 10). The second method (TAB 10) only uses 108 pounds of dry yeast every 8 hours compared with the 458 pounds needed by the two yeast tank set up shown in TAB 9. As shown in TAB 11, a 10 fermenter system needs 417 pounds of dry yeast each time, two 10,000 gallon yeast slurry tanks, two 62,749 gallon yeast tanks, and two 393,738 gallon yeast stage tanks, see cell B4:M22. TAB 12 compares alcohol percentage overtime using typical ICM systems and the LT2FEM method. LT2FEM cuts fermentation time by 8 to 10 hours (8 hours for 7 fermenter systems, and 10 hours for 10 fermenter systems). TAB 13 shows the amount of dry yeast, size of the yeast tank, and size of the yeast stage tank for optimized 4 to 10 fermenter systems using this method. This LT2FEM system uses additional yeast and yeast stage tanks but decreases total fermentation cycle time by up to 10 hours. This solution is perfect for converting a continuous fermentation system to a batch fermentation system as most continuous fermentation systems already have two large yeast tanks which can be used as yeast stage tanks as shown in TAB 9.

FIG. 5 illustrates a method 500 having a Continuous Yeast Propagation in a YST in accordance with some embodiments. The method 500 is embodied as LT3FEM: (Continuous Yeast Propagation in YST Method). This method 500 system uses a large yeast stage tank 504 to continuously propagate yeast and supply yeast solution from a yeast tank 502 for one or more fermenters 506. The yeast stage tank 504 can dump an ideal/optimized YCC solution to any selected fermenter tank 506. TAB 14 shows simulation data for a 7 fermenter system with an LT3FEM set up.

For LT3FEM, 121 pounds of dry yeast is added to 2900 gallons of water in the yeast slurry tank for two hours and then dumped to a yeast tank (87,834 gallon). The yeast tank is filled up with mash at a controlled mash rate (see cell C6:C23) to maintain an ideal YCC (>250*10^6) during the filling period. Yeast propagates in the yeast tank for 16 hours before dumping the yeast solution to a 326,122 gallon yeast stage tank. Mash rate to the yeast stage tank is controlled for the next 16 hours to maintain a maximum YCC (>250*10^6) (see cell F6:F23). The yeast stage tank can then be used to propagate more yeast by adding mash at a controlled rate while feeding optimized/ideal YCC solution to a fermenter (see cell K6:K22). With this method, the YCC in the fermenter is always at a maximum YCC during the filling period (see cell I6: I23), and the likelihood of yeast stress or bacterial spikes are greatly decreased.

As soon as the first fermenter of the fermenters 506 is filled, the yeast stage tank 504 can start dumping to another fermenter 506 while still continuing to intake mash 508. This continuous cycle of intaking mash 508 to the yeast stage tank 504 and sending ideal YCC solution to the next fermenter 506 without adding more dry yeast can continue indefinitely (See cell P15:P22).

TAB 14 shows simulation data for a 7 fermenter system using an LT3FEM system and TAB 15 shows data for a 10 fermenter system using an LT3FEM system. For the 10 fermenter system, yeast propagation time decreases to 10 hours using LT3FEM technology, so extra yeast propagation tanks (7,400 gallon yeast slurry tank, 46,434 gallons of the $1^{st}$ yeast tank, 291,306 gallons of the $2^{nd}$ yeast tank, and 492,400 gallons of a yeast stage tank are needed to maximize yeast cell counts to fermenters in a 10 fermenter system. In TAB 15, see cell B4:D19 for $1^{st}$ yeast tank (46,434 gallon) operation data, see cell E4:G19 for 2nd yeast tank (291,360 gallon) operation data, and see cell H4:L19 for yeast stage tank (492,408 gallon) data.

Comparing TAB 10 using LT2FEM with Tab 14 using LT3FEM for 7 fermenter systems and TAB 11 using LT2FEM with TAB 15 using LT3FEM for 10 fermenter systems, it is clear that the alcohol percentage production curve is about the same, but LT3FEM requires only one yeast tank and decreases yeast propagation costs. Thus, LT3FEM outperforms LT2FEM by cutting capital and operational costs. TAB 16 compares alcohol percentage over time between LT3FEM and currently used ICM systems. This shows the alcohol percentage using LT3FEM can be achieved with a 48 hour fermentation cycle. In contrast, the typically used ICM systems require 58 hours. TAB 17 summarizes yeast stage tank size, yeast tank size, yeast slurry tank size, and the amount of dry yeast needed for various fermentation systems (4 fermenter to 10 fermenter).

FIG. 6 illustrates a method 600 having a Yeast Solution Recycling system in accordance with some embodiments. The method 600 is embodied as LT4FEM (Yeast Solution Recycling Method), which provides an advantage of maintaining a maximum yeast cell count at all three tanks (yeast tank 602, yeast stage tank 604, and the fermenters 608).

The method 600 combines at least one large yeast stage tank 604 and cycles yeast 610 from one fermenter to the next fermenter of the fermenters 608. This way both yeast stage fermenter 604 and the fermenter tank 606 maintain ideal YCC during the filling period. TAB 18 shows simulation data for a 7 fermenter system with yeast solution cycled from fermenter #1 606 to fermenter #2 608A. This setup requires 14.6 pounds of dry yeast to be added to 350 gallons of water in the yeast slurry tank for two hours and then dumped to a 10,601 gallon yeast tank for a 16 hour yeast propagation cycle. During the yeast propagation cycle mash intake is controlled to maintain a maximum YCC while filling (See cell C13:C25). Once full, the yeast tank 602 dumps to a 321,067 gallon yeast stage tank 604 where mash 612 intake is adjusted to maintain a maximum YCC until the yeast stage tank 604 is full (see Cell F10:F22). The yeast stage tank 604 then sends ideal yeast solution to fermenter #1 606. The fermenter #1 606 continues to intake mash 612 maintaining the ideal YCC at all times (See cell K7:K14). Once fermenter #1 606 is full it can send yeast solution to fermenter #2 608A for three hours while continuing to intake mash 612. After three hours, mash flow switches to filling fermenter #2 608A until full while maintaining an ideal YCC. Using this solution, two fermenters are able to use the yeast solution from one yeast stage tank 604.

TAB 18 shows simulation data for a 7 fermenter system with this recycle system (yeast solution continuously transferred from one fermenter to the next) set up using a yeast tank (10,601 gallons) and a 321,067 gallon yeast stage tank. TAB 19 shows simulation data for a 10 fermenter system using LT4FEM. Because the filling time is only 5 hours for 10 fermenter systems, two yeast tanks (11,922 gallon and 74,810 gallon) are needed in series to produce enough yeast propagation for a 469,423 gallon yeast stage tank. TAB 20 compares alcohol percentage over time in 7 and 10 fermenter systems for LT3FEM, LT4FEM, and current 7 and 10 fermenter systems. This shows that a) an LT3FEM system cuts fermentation cycle time by 8 to 10 hours (8 hour for 7 fermenter systems and 10 hours for 10 fermenter systems) and b) an LT4FEM system cuts fermentation cycle time by 6 to 8 hours (6 hours for 7 fermenter systems, and 8 hours for 10 fermenter systems.) TAB 21 summarizes the amount of dry yeast, size of yeast slurry tank, size of yeast tank, and size of yeast stage tank for an LT4FEM system with various fermentation systems (between 4 and 10 fermenters). TAB 22 shows the minimum necessary size for a yeast stage tank for LT2FEM, LT3FEM and LT4FFEM systems. Basically, the minimum size for a yeast stage tank is 3.33 times the mash intake rate per hour to achieve a 30% yeast propagation rate. For a 25% yeast propagation rate the yeast stage tank must be 4 times the mash intake rate. For a 40% yeast propagation rate the yeast stage tank must be 2.5 times the mash intake rate.

FIG. 7 illustrates a method 700 having a Continuous Yeast Propagation in YST or Fermenter in accordance with some embodiments. The system of method 700 is embodied as LT5FEM (Continuous Yeast Propagation in YST or Fermenter Method). The method 700 combines the systems of LT3FEM and LT4FEM. Both LT3FEM and LT4FEM are able to use less dry yeast. LT3FEM uses continuous yeast propagation in a large yeast tank to feed multiple fermenters. LT4FEM recycles yeast solution by sending the solution from one fermenter to the next in line. These methods and systems significantly decrease capital and operational costs by reducing the dry yeast needed, and shortening the time for a full fermentation cycle. Recycling the yeast in these ways can increase the chance of infection.

However, field data suggests that it is safe to complete two passes of active yeast solution from a yeast stage tank 702 to a fermenter 706 or two passes from one fermenter 704 to another fermenter 706; or one pass from a yeast stage tank 702 to a fermenter 704/706 and one pass from one fermenter 704 to another fermenter 706 with this method before starting a new fermentation cycle. TAB 23 shows simulation data for a 7 fermenter system with one pass from yeast stage tank 702 to fermenter 706 using LT3FEM technology of continuous propagation in a minimum size yeast stage tank 702 (589,223 gallons) followed by one recycling pass using LT4FEM technology of recycling yeast solution which sends solution from one fermenter to another. TAB 24 shows simulation data for a 7 fermenter system with one pass (from yeast stage tank to fermenter) using LT3FEM with a maximum size yeast stage tank (789,990 gallons) followed by one recycling pass (from fermenter to fermenter) using the LT4FEM recycling method. This data shows that the larger yeast stage tank cuts fermentation time and decreases the chance of infection.

TAB 15 shows data for one pass using the LT3FEM method of continuous yeast propagation in a yeast stage tank and TAB 19 shows one recycling pass using the LT4FEM method of recycling solution from fermenter to fermenter. TAB 25 shows two passes with the first pass using LT3FEM technology (from yeast stage tank to fermenter) and the second pass using LT4FEM technology (fermenter to fermenter). TAB 26 shows two recycling passes using the LT4FEM set up of recycling yeast solution for a 10 fermenter system. TAB 27 shows two passes using the continuous yeast propagation setup of LT3FEM for a 10-fermenter system. The data shows that more passes using these technologies results in greater decreases to capital and operational costs, but can increase the chance of infection.

Figure 8:
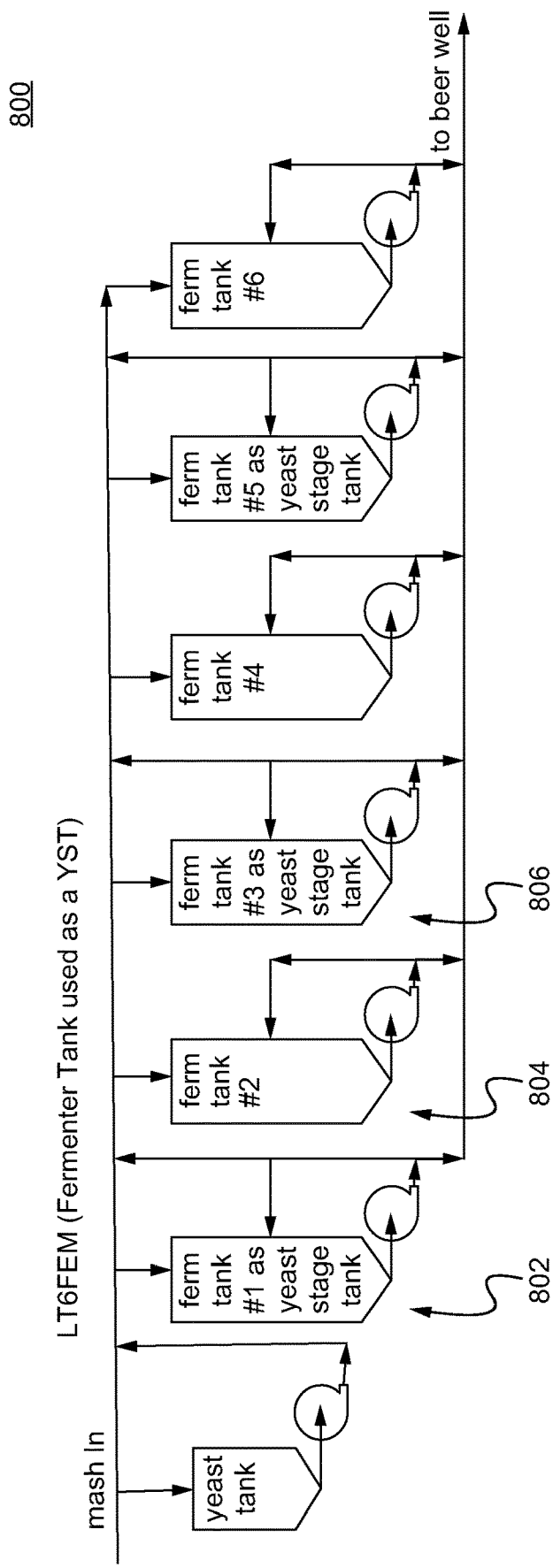
FIG. 8 illustrates using a fermenter tank used as a YST in accordance with some embodiments.

FIG. 8 illustrates a method 800 having a Fermenter Tank used as YST in accordance with some embodiments. The system of method 800 is embodied as LT6FEM (Fermenter Tank used as YST Method). In some embodiments, the above systems (LT1FEM to LT5FEM) all used one or more larger yeast stage tanks between the yeast tank and the fermenters. These systems can decrease capital costs, operational costs, and the work for operators to fill, dump and Clean-In-Place (CIP). FIG. 8 shows a yeast stage tank performing one pass of continuous yeast propagation to a fermenter. In some embodiments, this operation can continue for multiple passes. More passes increase savings in operational and capital costs, but also increases the chance of infection.

Figure 9:
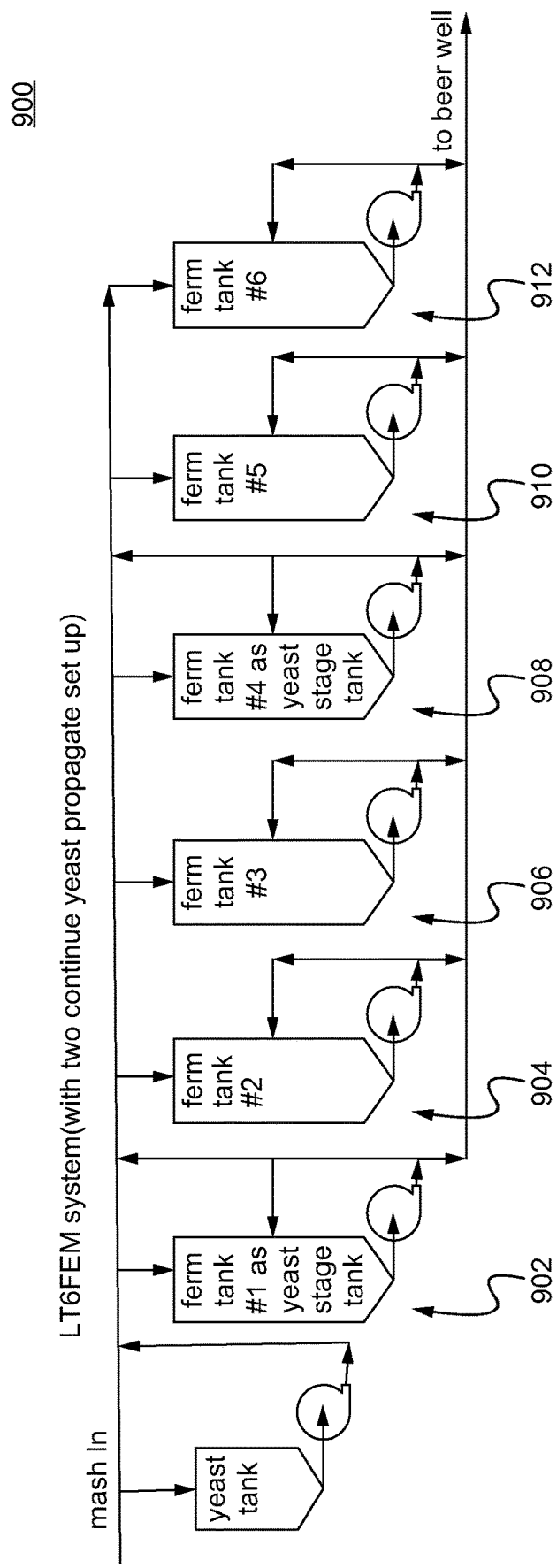
FIG. 9 illustrates using a fermenter tank used as a YST in accordance with some embodiments.

FIG. 9 shows a fermenter 902, which performs a continue yeast propagation twice for the fermenter 904 and 906. The fermenter 908 performs continue yeast propagate twice for fermenter 910 and 912.

Figure 10:
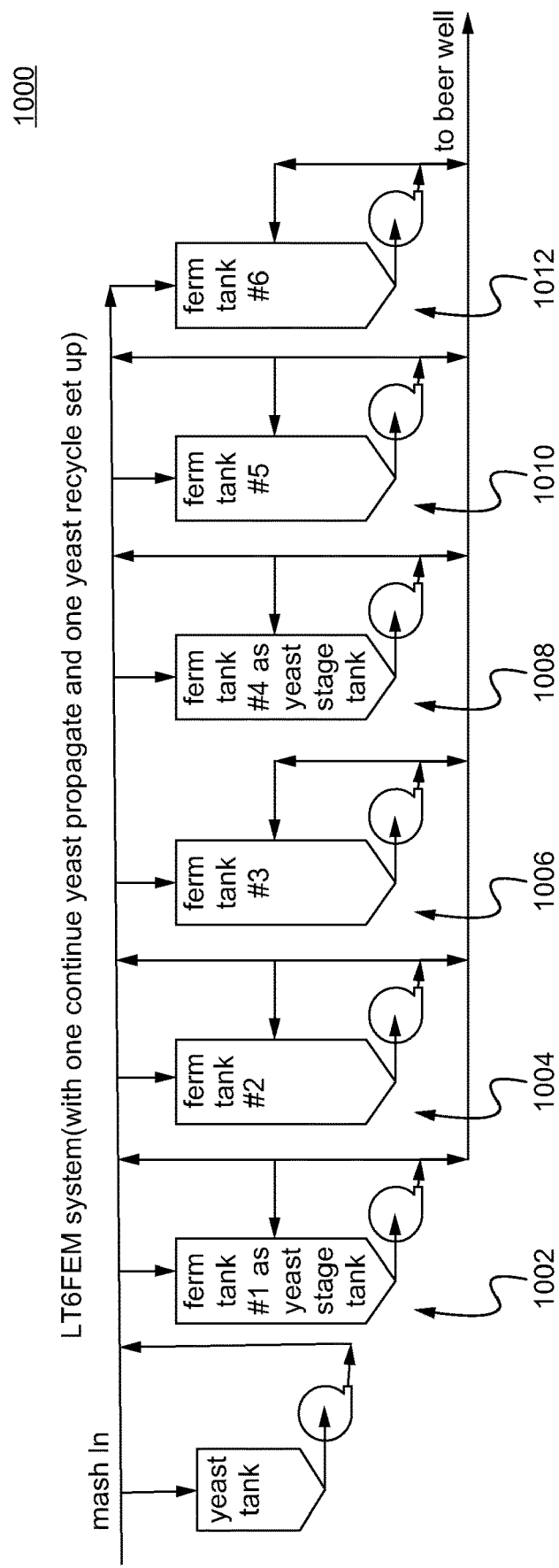
FIG. 10 illustrates using a fermenter tank used as a YST in accordance with some embodiments.

FIG. 10 show a fermenter 1002, which performs a continue yeast propagation to fermenter 1004, which is followed by yeast recycling from the fermenter 1004 to fermenter 1006. The ferment 1008 performs continue yeast propagation for fermenter 1010 followed by yeast recycling from fermenter 1010 to fermenter 1012.

The above FIGS. 8-10 illustrate some embodiments using one or more fermenters as the yeast stage tank (e.g., can be named as a fermenter as a yeast stage tank or "FYST"). In such cases, using the fermenter to perform the processes and functions of a yeast stage tank (e.g., yeast propagation), so that no additional yeast stage tank is needed. A yeast solution is first transferred from a yeast tank to the FYST. The yeast solution in the FYST is propagated to become a propagated solution. In some embodiments, the propagated yeast solution is continuously transferred from the one or more of FYST to one or more fermenters. In other embodiments, the propagated yeast solution is continuously transferred from the FYST to first fermenter and then transfers the solution from the first fermenter to the second or subsequent fermenters, which is referred as a recycling yeast process. Various processes paths and procedures are within the scope of the present disclosure.

In some embodiments, LT6FEM (the method 800) uses a fermenter 802 as a yeast stage tank to continuously propagate yeast for the next fermenter 804. Once the first fermenter 802 (donator fermenter) has supplied enough ideal yeast solution to the second fermenter 804 (receptor fermenter), then the first fermenter 802 stops acting as a yeast stage tank, and then the fermenter 802 is filled completely with mash and starts fermenting.

TAB 28 shows simulation data for a four fermenter system. Fermenters #1 802 and #3 806 are used as yeast stage tanks and propagate yeast to supply huge amounts of yeast solution for fermenters #2 804 and #4 806. Once done, Fermenters #1 802 and #3 806 are filled up with mash and act as fermenters. This allows the fermentation cycle to be complete in 48 hours. As shown in TAB 28, 6.46 pounds of dry yeast are added to 155 gallons of water in the yeast slurry tank with nutrients for two hours. This solution is then dumped to a 20,000 gallon yeast tank where mash is added at a rate to increase the total volume by 18.2 percent per hour (see cell C9:C38). This rate maintains the yeast cell count at a maximum ($250*10^6$).

After 32 hours of yeast propagation time, the yeast tank contains 19,781 gallons of ideal yeast cell count solution. This yeast solution with a maximum yeast cell count ($250*10^6$) is dumped to Fermenter #1 802 and mash is added to increase volume by 18 percent per hour. This allows the yeast cell count to remain ideal. After 16 hours the total volume in fermenter #1 802 will be 281,135 gallons (see H7:H22). Fermenter #1 802 acts like a yeast stage tank by continuously propagating yeast for another 16 hours to supply a huge amount of ideal yeast solution to fermenter #2 (see cell H23:H38, M23:M38). Then fermenter #1 802 fills up with mash and acts as a fermenter (see cell H39:H54). During this filling up period fermenter #3 806 will start acting as a new yeast stage tank (see cell R39:R54).

TAB 28 shows a yeast stage tank doing one pass of continuous yeast propagation to a fermenter. However, this operation can continue for multiple passes. More passes increases savings in operational and capital costs but also increases the chance of infection. TAB 28A shows the LT6FEM system cuts alcohol production lag time by around 10 hours. Thus, the LT6FEM system can operate on a 48-hour (2 day) fermentation cycle instead of the current 56 hour cycle. TAB 28 also shows that with a 20,000 gallon yeast tank, the LT6FEM system can maintain maximum yeast cell count for any yeast that has a yeast growth rate over 18.2 percent per hour. Normal yeast growth rate is around 25 to 30 percent.

The LT6FEM simulation data for 4 to 10 fermenter systems with filling times between 5 and 16 hours, variable yeast tank sizes, and different yeast growth rates is summarized in TAB 29. For a current 7 fermenter system (800,000 gallon tanks) with 8 hour filling time, the mash intake rate is 100,000 gallons per hour (GPH). For a yeast growth rate of 30% (see cellD16:C22), the minimum yeast tank size is 40,000 gallons (0.4*100,000) and the minimum yeast stage tank capacity is 329,000 gallons (3.29*100,000). If yeast growth rate is only 25%, like typical GMO yeast, then the yeast tank must be 65,000 gallons (0.65*2100,000) and yeast stage tank capacity is 386,000 gallons (3.86*100,000). Clearly, a larger yeast tank is needed for lower yeast growth rate unless a new system is designed like the LT6FEM system.

Using the LT6FEM method for a 8 fermenter system with 7 hour filling time, it is able to be operated it like 2 four fermenter systems with 14 hour filling times but staggered by 7 hours. Similarly, a 10 fermenter system with 5.5 hour filling times can operate as two 5 fermenter systems with 11 hour filling times but staggered by 5.5 hours. The split mash flow concept used in LT1FEM can also be incorporated into LT6FEM. TAB 29 compares results for 8 fermenter systems (cell E13:I22 against cell F24:I32), and ten fermenter systems (cell B24:E33 against cell J24:M33). TAB 29 also shows that treating 8 and 10 fermenter systems as two 4 and 5 fermenter systems allows the use of a smaller yeast tank but leads to lower alcohol percentage and requires longer fermentation time.

TAB 30 shows the alcohol percentage in the fermenter during the first 18 hours and shows that higher alcohol contents achieved with larger yeast tanks and yeast stage tanks. TAB 31 shows yeast tank sizes needed for various filling times and yeast growth rates. Larger yeast tanks are needed where the yeast growth rate is slower or where filling time is shorter. TAB 32 shows the yeast stage tank size needed for various filling times and yeast growth rates. Larger yeast stage tanks are needed where yeast growth rate is slower or where filling time is shorter. The maximum size of a yeast stage tank is the same as the size of a fermenter tank.

TAB 33 shows average alcohol percentage at hour 18 based on various filling times and yeast growth rates. Lower yeast growth rates and shorter filling times require a larger yeast tank and yeast stage tank to increase alcohol percentage in the fermenter.

TAB 34 shows the fermentation time reduced by 6 to 17 hours depending on the size of the yeast tank and yeast stage tank. Maximum yeast tank size and maximum yeast stage tank size (same size as fermenter) will give the shortest fermentation time cutting fermentation time by 17 hours for a 4 fermenter system and by 13 hours for a 10 fermenter system. TAB 35 shows the amount of dry yeast needed dependent on filling times and yeast growth rates. More dry yeast is needed for shorter filling times or slower yeast growth rates.

The above analysis is based on fermenter systems where the yeast stage tank acts as a continuous yeast propagation tank and supplies huge amounts of ideal yeast solution for one pass. However, when more than one pass can be completed/performed without infection problems, further decreasing operational costs are achieved. Factors like system design, bacterial control, type of yeast, and operational conditions determine how many passes can be completed without significantly increasing the risk of infection. More passes using continuous yeast propagation increase savings in yeast propagation cost and enzyme cost.

TAB 36 compares alcohol percentage in a 7 fermenter system after different numbers of passes. TAB 37 compares the alcohol percentage at hour 18 in a 7 fermenter system relative to the amount of dry yeast used the number of passes. The data shows that an LT6FEM system using a maximum size yeast tank and maximum size yeast stage tank for multiple passes is ideal. LT6FEM benefits include: a) it produces less unwanted byproducts like glycerol (less than 1% glycerol when finished with fermentation), b) it increases alcohol yield by up to 3% over current batch systems, c) it decreases bacterial infection problems, d) it stabilizes operation, leading to less variability, e) it decreases yeast propagation costs by more than 90%, and f) it decreases enzyme costs by more than 30%.

The data shows that a larger yeast stage tank gives better results and leads to a more stable operation. But this solution requires a larger yeast tank and more dry yeast. For an LT6FEM system, the maximum yeast stage tank size is the same as the fermenter tank size. TAB 38 shows the yeast tank size needed for a maximum size yeast stage tank depending on the yeast growth rate. TAB 39 shows the average alcohol percentage at hour 18 for various yeast growth rates when the yeast stage tank is the same size as a fermenter. TAB 40 shows the decrease in fermentation time needed for various yeast growth rates when a maximum size yeast stage tank is used. TAB 41 shows the amount of dry yeast needed for various yeast growth rates when a maximum size yeast stage tank is used.

TAB 29 to TAB 35 show the minimum yeast stage tank size needed to maintain the ideal yeast cell count at all times. TAB 38 to TAB 41 show results for a maximum size yeast stage tank (same size as a fermenter tank). The LT6FEM system improves operation with a yeast stage tank that is between the minimum and maximum size detailed. The impact of the yeast stage tank size depends on the size of the yeast tank (amount of yeast solution sent to the yeast stage tank). An additional benefit of this technology is operation stability. Yeast growth rate can vary greatly but the LT6FEM system works even with lower yeast growth rates. Slower yeast growth stabilizes operation, decreases chance of infection, and decreases chance of yeast stress.

For very large fermentation systems, such as the typical ICM 8 to 10 fermenter systems, the filling time is very short (5 to 7 hours). Thus, there is not enough time for the yeast tank and the yeast stage tank to provide a sufficient volume of the ideal yeast cell count solution to the next fermenter. LT6FEM solves this problem by treating the system as two or even three smaller systems. For example, TAB 42 shows that the typical ICM 10F5H system (10 fermenter system with a 5 hour filling time) can operate as two 5 fermenter systems with 12 hour filling times as shown in program 22LTtwo5F12H1P0.3 5.73 0.28 or three 3 fermenter systems are able to be formed with 18 hour filling times as shown in program 22LTthree 3F18H2P0.44 11.7 0.2.

Increasing fill time allows the use of smaller yeast tanks and yeast stage tanks. The Lee Tech Fermentation Simulator can consider all the variables and optimize any customer's fermentation system. The Simulator shows that there are some optimum relationships between the size of the yeast tank, the yeast stage tank and fermentation time. The Lee Tech Fermentation Simulation program is a very useful tool for finding the optimum fermentation system for any customer.

The above six LTFEM technologies (LT1FEM to LT6FEM) have different advantages and disadvantages. Each system is ideal for meeting specific challenges in existing fermentation systems. However, the best system is LT6FEM which has the greatest reduction in operational and capital costs. In the disclosure, the term LT # FEM refers to the type number of exemplary embodiments. In some embodiments, the fermenters can be split into two or more groups. In some embodiments, 10 fermenters with filling time of 5.5 hours can be split into two 5 fermenter tanks (e.g., in parallel lines) with filling time of 11 hours. In a case of 9 fermenter tanks, three lines of 3 fermenter tanks each line. Any other manners of splitting the total number of fermenter tanks are within the scope of the present disclosure.

Using continuous yeast propagation or yeast recycling methods to get large amounts of yeast solution to a fermenter has been described in a previous patent application, U.S. Provisional Patent Application Ser. No. 62/044,092, filed Aug. 29, 2014 and titled, "NEW IMPROVEMENT FERMENTATION SYSTEM FOR DRY MILL PROCESS". However, without a large yeast stage tank, the yeast cell count (YCC) in the 1st fermenter (or donator fermenter) drops too low causing yeast stress (which can result in unwanted byproducts like glycerol) and bacterial infections (resulting in another unwanted byproduct, lactic acid). Larger yeast stage tanks need more time to reach the ideal YCC solution. As shown, combining continuous yeast propagation or yeast recycling with a large yeast stage tank decreases operational and capital costs. The computer simulation can show the optimal yeast propagation strategies, yeast tank sizes and quantity, yeast stage tank size and design, and the amount of dry yeast needed. This detailed information is extremely useful for every dry mill plant.

The purpose of splitting the mash flow is ensuring the yeast cell count in the yeast tank and fermenter tanks have a maximum yeast cell count (>250*10^6) and maintain a higher percentage of alcohol to suppress bacterial growth.

In utilization, the methods and systems disclosed herein are used to provide an optimized yeast solution to the fermentation tanks for fermentation processes.

In operation, a yeast stage tank is used to prepare the yeast solution to a predetermined condition before adding to the fermenters.

What is claimed is:

1. A fermentation process using a yeast stage tank comprising:
   a. transferring a first yeast solution having a yeast content less than 5 g weight per liter from a yeast tank to the yeast stage tank;
   b. continuously adding mash and maintaining a maximized yeast cell count greater than 250*10^6 cells/ml in the yeast stage tank for an entire filling period;
   c. using the yeast stage tank as a continuing yeast propagation tank to produce a propagated active yeast solution for a fermenter tank during the filling period to maintain the maximized yeast cell count in both the yeast stage tank and the fermenter tank; and
   d. transferring the propagated active yeast solution from the yeast stage tank to the fermenter tank when the transferring of the propagated active yeast solution results in a yeast cell count greater than 250*10^6 cells/ml in both the yeast stage tank and the fermenter tank for the entire filling period.

2. The fermentation process of claim 1, further comprising continuously transferring the propagated active yeast solution from the yeast stage tank to multiple fermenter tanks.

3. The fermentation process of claim 1, further comprising dumping an entire batch of a remaining propagated active yeast solution from the yeast stage tank to a coming fermenter tank after a predetermined number of fermenter tanks are full.

4. The fermentation process of claim 3, further comprising performing a clean-in-place (CIP) process after the dumping the entire batch of the remaining propagated active yeast solution to the coming fermenter tank.

5. The fermentation process of claim 4, further comprising intaking a second yeast solution from the yeast tank to the yeast stage tank and restarting propagating the second yeast solution in the yeast stage tank.

6. The fermentation process of claim 1, wherein the yeast stage tank has a size sufficiently large to maintain a yeast cell count>250*10^6 cells/ml for an entire filling process in both the yeast stage tank and the fermenter tank.

7. The fermentation process of claim 1, wherein the yeast stage tank has a size, which is provided as a function of a yeast propagation rate and a mash supplying rate.

8. The fermentation process of claim 7, wherein the size of the yeast stage tank is at least 3.3 times of an hourly mash supplying amount when a cell count of a yeast increases 30% per hour.

9. The fermentation process of claim 7, wherein the size of the yeast stage tank is at least 4 times of an hourly mash supplying amount when a cell count of a yeast increases 25% per hour.

10. The fermentation process of claim 1, further comprising keeping a food-to-yeast ratio represented by a formula of % DT/% yeast by weight below 4 for the entire filling period of the yeast stage tank.

11. The fermentation process of claim 10, further comprising keeping a glucose level below 2% during the entire filling period of the yeast stage tank.

12. The fermentation process of claim 1, wherein propagating the first yeast solution in the yeast stage tank to the propagated active yeast solution resulted in a reduced needed amount of a yeast from the yeast tank.

* * * * *